United States Patent [19]

Crabbé et al.

[11] 3,970,684

[45] July 20, 1976

[54] POLYUNSATURATED PROSTAGLANDIN DERIVATIVES

[75] Inventors: Pierre Crabbé, Grenoble, France; John H. Fried, Palo Alto, Calif.; Angel Guzman, Mexico City, Mexico

[73] Assignee: Syntex (U.S.A.) Inc., Palo Alto, Calif.

[22] Filed: July 15, 1974

[21] Appl. No.: 488,595

Related U.S. Application Data

[62] Division of Ser. No. 377,106, July 6, 1973, Pat. No. 3,873,598.

[52] U.S. Cl. ............... 260/468 D; 260/240 R; 260/468 G; 260/469; 260/473 G; 260/484 R; 260/485 L; 260/486 R; 260/487; 260/488 R; 260/501.1; 260/501.11; 260/501.17; 260/514 D; 424/305; 424/317; 260/471 R
[51] Int. Cl.² ................... C07C 61/38; C07C 69/74
[58] Field of Search ..................... 260/514 D, 468 D

[56] References Cited
UNITED STATES PATENTS
3,847,967   11/1974   Lincoln et al. ..................... 260/408

Primary Examiner—Robert Gerstl
Attorney, Agent, or Firm—Gerard A. Blaufarb; William B. Walker

[57] ABSTRACT

Novel prostaglandin dehydro analogs of the PGA and PGB series and the 9-hydroxy-derivatives thereof, which possess a diethylenic unsaturation in the carboxylic acid chain and may be additionally substituted at C-4, C-6, C-9 and/or C-15 by a methyl, ethyl or propyl group, as well as the C-20-nor, bisnor or C-20 alkyl derivatives thereof, the alkyl group being of a straight chain and containing from 1 to 5 carbon atoms inclusive,, and processes for making same. 9-keto-15α-hydroxyprosta-4,5,10,13-trans-tetraenoic acid and 9-keto-15α-hydroxyprosta-4,5,8(12),13-trans-tetraenoic acid are representative of the class. Also included are the pharmaceutically acceptable, non toxic esters and salts of the carboxylic acid function and the pharmaceutically acceptable, non toxic esters and/or ethers of the secondary hydroxyl groups. These compounds possess prostaglandin-like activities and thus are useful in the treatment of mammals, where prostaglandins are indicated.

19 Claims, No Drawings

POLYUNSATURATED PROSTAGLANDIN DERIVATIVES

This is a division of application Ser. No. 377,106, filed July 6, 1973, now U.S. Pat. No. 3,873,598, The present invention relates to certain novel prostaglandin derivatives of the PGA and PGB series and to a process for the production thereof.

More particularly, the present invention relates to prosta-4,5,10,13-trans-tetraenoic acid derivatives and prosta-4,5,8(12),13-trans-tetraenoic acid derivatives having oxygenated functions at C-9 and C-15 positions of the molecule, which may be further substituted at C-4, C-6, C-9 and/or C-15 by a methyl, ethyl or propyl group, to the C-20-nor, bisnor or C-20 alkyl derivatives thereof, the alkyl group being of a straight chain and containing from 1 to 5 carbon atoms inclusive. Also encompassed are the corresponding pharmaceutically acceptable, non toxic esters and salts of the carboxylic acid function, and the pharmaceutically acceptable, non toxic esters and ethers of the secondary hydroxyl groups.

Prostaglandins are members of a new hormonal system with a remarkable range of biological and pharmaceutical properties. These compounds belong to a group of chemically related 20-carbon chain hydroxy fatty acids containing a five membered ring in the structure and different degrees of unsaturation, a number of which have been reported in the literature. For a review on prostaglandins and the definition of primary prostaglandins, see for example S. Bergström, *Recent Progress in Hormone Research*, 22, pp. 153–175 (1966) and *Science*, 157, page 382 (1967) by the same author.

Prostaglandins are widely distributed in mammalian tissues and have been isolated from natural sources in very small amounts. In addition, a number of the naturally occurring prostaglandins have been prepared by chemical synthesis; note for example, *J. Am. Chem. Soc.*, 91 page 5675 (1969); *J. Am. Chem. Soc.*, 92, page 2586 (1970) and *J. Am. Chem. Soc.*, 93, pages 1489–1493 (1971) and references cited therein, W. P. Schneider et al., *J. Am. Chem. Soc.* 90, page 5895 (1968); U. Axen et al., *Chem. Commun.*, page 303 (1969) and W. P. Schneider, *Chem. Commun.*, page 304 (1969).

Because of the remarkable range of biological and pharmacological properties exhibited by this family of compounds, a great deal of interest has focused upon such compounds, and the preparation of analogs of such compounds; accordingly, we have discovered processes and intermediates for preparing modified prostaglandins and derivatives thereof.

The novel prostaglandin derivatives of the present invention can be represented by the following formulas:

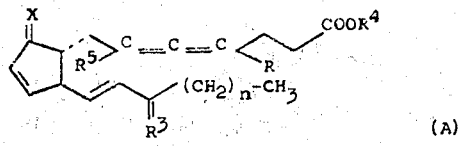

(A)

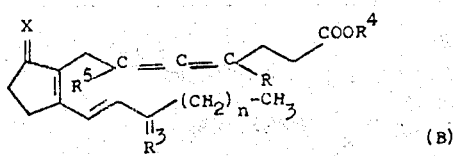

(B)

wherein
X represents a keto group, the grouping

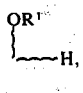

in which $R^1$ is hydrogen or a conventionally hydrolyzable ester or ether group, or the grouping

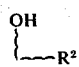

in which $R^2$ is methyl, ethyl or propyl;

each of R and $R^5$ represents hydrogen, methyl, ethyl or propyl; $R^3$ represents the grouping

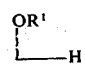

in which $R^1$ has the above indicated meaning, or the grouping

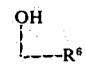

in which $R^6$ is methyl, ethyl or propyl;

$R^4$ represents hydrogen, a lower alkyl group of 1 to 3 carbon atoms or the pharmaceutically acceptable, non-toxic salts of compounds in which $R^4$ is hydrogen and $n$ is an integer of from 2 to 9:

provided that when $R^2$ is $\alpha$ the hydroxyl group, attached to the same carbon atom as $R^2$, is $\beta$; and when $R^2$ is $\beta$ the hydroxyl group, attached to the same carbon atom as $R^2$, is $\alpha$; and when $R^6$ is $\alpha$ the hydroxyl group, attached to the same carbon atom as $R^6$, is $\beta$; and when $R^6$ is $\beta$ the hydroxyl group, attached to the same carbon atom as $R^6$, is $\alpha$.

The dotted lines shown in the above formulas and in the formulas below indicate that the substituents are in $\alpha$ configuration, i.e., below the plane of the cyclopentane ring.

The wavy lines ( ) indicate the $\alpha$ or $\beta$ configuration, or mixtures thereof.

The double bond at C-13 in the compounds of the present invention has the same configuration as in natural prostaglandins of the $PGE_1$, $PGE_2$, $PGF_{1\alpha}$ or $PGF_{2\alpha}$ series, that is, the trans configuration.

The preferred meaning of $n$ is 4 i.e., the preferred compounds of the invention are those having the usual C-20 carbon unit structure of natural prostaglandins.

These novel compounds possess asymmetric centers and thus can be produced as racemic mixtures. The racemic mixtures can be resolved if desired, at appropriate stages by methods known to those skilled in the art, to obtain the respective individual antimers. It is to be understood that the individual antimers as well as mixtures of such antimers are encompassed within the scope of the present invention.

Compounds of formula (A) cover the individual antimers particularly the 8R-antimers, and racemic mixtures as well, while compounds of formula (B) refer to racemates.

When the compounds of formula (A) are racemic mixtures, they are produced starting from racemates, while when the compounds of formula (A) are individual antimers the compounds are preferably obtained starting from the appropriate individual antimer.

For the sake of simplicity only one antimer of each pair will be depicted in the description of the process and Claims; however, it is to be understood that the mirror images for the racemic mixtures and the individual antimers are also encompassed thereby.

The use of the symbol "R" preceding a substituent designates the absolute stereochemistry of that substituent according to the Cahn-Ingold-Prelog rules [see Cahn et al., *Angew. Chem. Inter. Edit.*, Vol. 5, p. 385 (1966), errata p. 511; Cahn et al., *Angew. Chem.*, Vol. 78, p, 413 (1966); Cahn and Ingold, *J. Chem. Soc.* (London), 1951, p. 612; Cahn et al., *Experientia*, Vol. 12, p. 81 (1956); Cahn. *J. Chem. Educ.*, Vol. 41, p 116 (1964)]. Because of the interrelation of the designated substituent with the other substituents in the compound having $\alpha$ or $\beta$ prefixes, the designation of the absolute configuration of one substituent fixes the absolute configuration of all substituents in the compound and thus the absolute configuration of the compound as a whole.

The term "conventionally hydrolyzable esters or ethers" as used herein refers to those physiologically acceptable hydrolyzable ester and ether groups employed in the pharmaceutical art which do not significantly adversely affect the pharmaceutical properties of the parent compound. The conventionally hydrolyzable esters are derived from hydrocarbon carboxylic acids. The term "hydrocarbon carboxylic acid" defines both substituted and unsubstituted hydrocarbon carboxylic acids. These acids can be completely saturated or possess varying degrees of unsaturation (including aromatic), of straight chain, or cyclic structure, and preferably contain from one to 12 carbon atoms. In addition, they can be substituted by functional groups, for example, hydroxy, alkoxy containing up to 12 carbon atoms, nitro, amino, halogeno, and the like, attached to the hydrocarbon backbone chain. Typical conventional hydrolyzable esters thus included within the scope of the term and the instant invention are acetate, propionate, butyrate, valerate, caproate, enanthate, caprylate, pelargonate, acrylate, undecenoate, phenoxyacetate, benzoate, phenylacetate, diphenylacetate, diethylacetate, trimethylacetate, t-butylacetate, trimethylhexanoate, methylneopentylacetate, cyclohexylacetate, cyclopentylpropionate, adamantoate, glycolate, methoxyacetate, hemisuccinate, hemiadipate, hemi-$\beta,\beta$-dimethylglutarate, acetoxyacetate 2-chloro-4-nitro-benzoate, aminoacetate, diethylaminoacetate, piperidinoacetate, $\beta$-chloropropionate, trichloroacetate, $\beta$-chlorobutyrate, bicyclo-[2.2.2]-octane-1-carboxylate, 4-methyl-bicyclo-[2.2.2]-oct-2-ene-1-carboxylate and the like. The preferred conventional hydrolyzable ester is acetate.

"Conventional hydrolyzable ethers" include the tetrahydrofuran-2-yl, tetrahydropyran-2-yl and 4-methoxytetrahydropyran-4-yl ethers.

The addition salts are derived from pharmaceutically acceptable basic salts, including metal salts such as sodium, potassium, calcium, magnesium, aluminum and the like, as well as organic amine salts such as ammonium, triethylamine, 2-dimethylamino ethanol, 2-diethylamino ethanol, tris(hydroxyethyl) amine, lysine, arginine, caffeine, procaine, N-ethylpiperidine, hydrabamine and the like. The term "pharmaceutically acceptable" refers to salts which do not significantly adversely affect the properties of the parent compound.

The novel prostaglandin derivatives of the present invention can be obtained by a process illustrated by the following sequence of reactions:

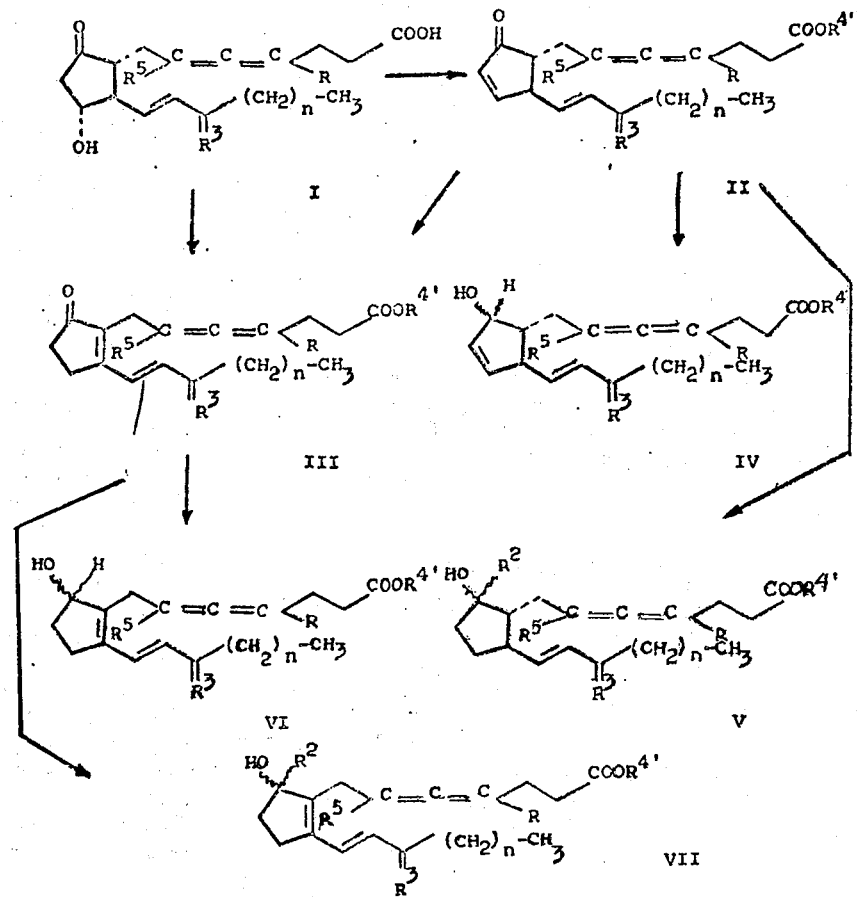

wherein R, $R^2$, $R^3$, $R^5$ and $n$ have the above-indicated meaning and $R^{4'}$ represents hydrogen or a lower alkyl group, particularly the methyl group.

Formula (A) is a composite of formulas II, IV and V (racemic mixtures and individual antimers) and formula (B) is a composite of formulas III, VI and VII (racemic compounds).

In practicing the process outlined above, a 9-keto-11α-hydroxy prostatrienoic acid derivative of formula I (racemate or 8R-antimer) is dehydrated under mild alkaline conditions, to produce the corresponding 10-dehydro derivative of formula II ($R^{4'}$ = H). This reaction can be effected with dilute solution of an alkali metal hydroxide, alkali metal carbonate or alkali metal bicarbonate in a lower aliphatic alcohol as solvent, in the presence of water. In the preferred embodiments, the dehydration is effected using a dilute alkali metal hydroxide solution such as a 1N sodium hydroxide solution in aqueous methanol, at a temperature comprised between about 0°C to room temperature, for a period of time of about 30 minutes to 1 hour, under an inert atmosphere, i.e., under argon or nitrogen atmosphere. The course of the reaction can be followed by t.l.c. or by periodic determination of the ultraviolet spectrum, the compound of formula II absorbing at 217 mμ. The reaction is interrupted when a peak at 278 mμ appears, which indicates that compound III begins to form. The product is isolated from the reaction mixture by dilution with water and acidification to liberate the free acid, extraction of the prostatetraenoic acid from the aqueous mixture with an organic solvent immiscible with water, e.g., methylene chloride, ether, chloroform, ethyl acetate and the like, evaporation of the organic extract and purification of the residue by chromatography on silica gel or thin layer chromatography. In the case of compounds having a secondary hydroxyl group at C-15 (II,

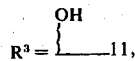

$R^{4'}$ = H), the acidification is preferably effected with dilute hydrochloric acid, to pH-2 while when the starting materials possess the grouping

at C-15, the acidification is effected with a weak acid such as acetic acid, oxalic acid and the like, to avoid dehydration at such position.

The transformation of compounds of formula I

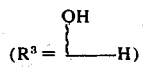

into compounds of formula II

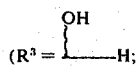

$R^{4'}$ = H) can be alternatively effected by mild acid treatment, e.g., by treatment with acetic acid in the presence of water using preferably 90% aqueous acetic acid. In the preferred embodiments, this alternative dehydration is effected at about 60°C to 65°C., for a period of time of about 18 hours, under argon or nitrogen atmosphere, however, these conditions are not critical, as the reaction can be conducted at higher or lower temperatures for shorter or longer reaction times, depending upon the temperature at which the reaction takes place. The product is isolated from the reaction mixture by dilution with water, extraction with a solvent immiscible with water, evaporation and purification of the residue by chromatographic techniques, as previously mentioned.

By a further alkaline treatment of a racemic or 8R-antimeric compound II ($R^{4'}$ = H) with sodium hydroxide, for an additional period of 6 to 8 hours at room temperature under an inert atmosphere, there is produced the corresponding racemic prosta-4,5,8(12), 13-trans-tetraenoic acid derivative of formula III ($R^{4'}$ = H). These compounds can also be obtained directly from the 9-keto-11α-hydroxy compounds of formula I, allowing the reaction with base to proceed for about 8 to 15 hours, at room temperature, or for 1 to 3 hours at 35°–40°C.

Compounds of formulas II or III ($R^{4'}$ = H) are then converted into an alkyl ester, preferably into the methyl ester, by conventional treatment with a diazoalkane such as diazomethane, at room temperature for a short period of time, of the order of 30 minutes to 1 hour, and the alkyl ester thus obtained reduced with sodium borohydride in methanol solution to produce a mixture of the corresponding 9α and 9β-hydroxylated compounds of formulas IV or VI ($R^{4'}$ = Me) respectively, which can be separated by chromatography on silica gel, to obtain the individual isomers in pure form. This reduction is conducted at about 0°C to room temperature, for a period of time of about 30 minutes to 1 hour.

By reaction of an alkyl ester compound of formulas II or III ($R^{4'}$ = Me) with an excess of an alkylmagnesium halide, i.e., using methyl-, ethyl- or propylmagnesium bromide or chlorides there are obtained the corresponding 9 -hydroxy-9 -alkyl prostatetraenoic acid compounds of formula V or VII ($R^{4'}$ = Me), respectively. This reaction is preferably effected in ether or tetrahydrofuran solution, using from 6 to 18 molar equivalents of the Grignard reagent per molar equivalent of starting compound, at a temperature of between −25°C to room temperature, for a period of time of 1 to 10 hours, under an inert atmosphere. In the preferred embodiments, the reaction is conducted by adding the reagent to a previously cooled solution (−25°C) of the 9-keto starting compound in diethyl ether solution under argon or nitrogen atmosphere, stirring the reaction mixture at 0°–5°C and following the course of the reaction by thin layer chromatographic techniques, the reaction being generally complete within about 8 hours.

Alternatively, the reaction can be carried out using an alkyllithium as reagent i.e., methyl-, ethyl or propyllithium, at about −70°C to about −20°C for about 10 to 30 minutes, using between 1.1 to 3 molar equivalents of the alkyllithium reagent, however, better results are obtained when using a Grignard reagent.

The product is isolated from the reaction mixture by conventional techniques, such as dilution with ammonium chloride solution, extraction, evaporation of the solvent and purification of the residue by chromatography, to separate the 9α-alkyl-9β-hydroxy and 9β-alkyl-9α-hydroxy isomers.

The methyl ester compounds of formulas IV, V, VI and VII ($R^{4'}$ = Me) are converted into the respective free acids of the invention (IV, V, VI and VII, $R^{4'}$ = H) by using enzymes in aqueous solutions. For this enzymatic hydrolysis, there is preferably used a crude pancreatic lipase commercially available (Sigma Steapsin), however, other enzyme systems which are known as useful for the hydrolysis of compounds unstable to alkaline or acid conditions can also be practical. Other lipases obtainable from bacterial sources, such as the partially purified lipase obtained from *Corynebacterium acnes* culture supernatant can also be used, or a lipase of those that are known to act on water insoluble esters of long chain fatty acids [L. Sarda et al. *Biochem. Biophys. Acta*. 23, 264 (1957)]. or baker's yeast [c. J. Sih et al., *J. C. S. Chem. Comm*. 240 (1972)]. Alternatively, the hydrolysis of the alkyl ester group can be achieved with the enzymes contained in the gorgonian Plexaurea homomalla (Esper).

The enzymatic hydrolysis with a crude pancreatic lipase can be conducted in a buffered aqueous solution containing sodium chloride and calcium chloride, at a neutral or almost neutral pH, at a temperature of between 22° to 30°C, preferably at about 25° to 27°C., adjusting the pH of the reaction mixture to 7.2 to 7.4 by addition of, for example, dilute sodium hydroxide solution, at intervals. The starting methyl ester compound of formulas IV, V, VI or VII ($R^{4'}$ = Me) is dissolved in the previously prepared buffered lipase aqueous solution by sonication at about 37°C using from about 0.5 ml. to about 1 ml. of the lipase solution per milligram of substrate. The methyl ester group is readily hydrolyzed within a short period of time, of the order of 5 minutes to 1 hour. The course of the reaction can be followed by thin layer chromatography; when the hydrolysis is complete, the free acid can be isolated from the reaction mixture by conventional techniques, such as acidification with a dilute acid solution, e.g., using dilute hydrochloric or acetic acid, extraction with a solvent immiscible with water, evaporation of the solvent an purification of the crude product by chromatographic techniques.

The hydrolysis with the enzymes contained in the residue of the gorgonian Plexaura homomalla, (after extraction of its content of prostaglandins of the $A_2$ and $B_2$ series) is conducted in the same aqueous solution used in the case of the hydrolysis with the crude pancreatic lipase, employing from about 5 to about 20 parts by weight of dry, finely ground gorgonian residue per one part of the alkyl ester to be hydrolyzed, stirring the reaction mixture at a temperature of between 20°C to 37°C, preferably at about room temperature, for a period of time of the order of 16 to 24 hours, at a pH of 7.5–7.7. When the hydrolysis is complete, as demonstrated by thin layer chromatographic analysis, the reaction mixture is diluted with acetone, acidified to pH 4 and the insoluble material separated by filtration. The product is isolated from the filtrate by concentration to a small volume, extraction with a solvent immiscible with water, evaporation and chromatographic purification, as described hereinbefore.

Compounds of formulas VI and VII having a secondary hydroxyl group at C-15

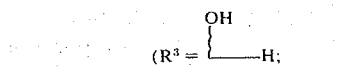

$R^{4'}$ = Me) can also be hydrolyzed by chemical methods using an alkali metal hydroxide or alkali metal carbonate, under nitrogen or argon atmosphere. The saponification with an alkali metal hydroxide, e.g., sodium or potassium hydroxide is preferably conducted at about room temperature for about 1 to 3 hours, while the reaction with sodium or potassium carbonate is carried out at a temperature above room temperature, of the order of about 30°C to 50°C, preferably at about 40°C, for a period of time of about 12 to 20 hours, preferably for about 16 hours. After acidification there is obtained the respective free acid, which is isolated from the reaction mixture by conventional techniques, such as by extraction with a solvent immiscible with water, evaporation of the solvent and purification of the residue by thin layer chromatography.

The secondary hydroxyl groups in the compounds of the present invention can be esterified in a conventional manner, to produce mono- or diesters, depending upon the particular prostaglandin derivative. Esterification can be accomplished by reaction of the hydroxylated compound with a carboxylic acid anhydride or chloride of less than 12 carbon atoms in pyridine solution.

Compounds of formulas II, III, IV and VI ($R^3$=α-hydroxy-β-hydrogen) can also be etherified by conventional techniques, to produce mono- or diethers. For example, reaction with dihydropyran, dihydrofuran, or 4-methoxy-5,6-dihydro-2H-pyran in an inert solvent such as, for example, methylene chloride or benzene and in the presence of an acid catalyst, e.g. p-toluenesulfonic acid or p-toluenesulfonyl chloride produces the tetrahydropyran-2'-yloxy, tetrahydrofuran-2'-yloxy or 4'-methoxytetrahydropyran-4'-yloxy derivatives, respectively.

Although the esterification or etherification reactions are usually effected using an excess of the esterifying or etherifying agents, it is preferable to use at least one molar equivalent of said reagents per hydroxyl group present in the starting compound.

The ethyl and propyl esters of the carboxylic acid function can be prepared by treatment of the free acid with an excess of a diazoalkane, i.e., diazoethane or diazopropane in ether or methylene chloride solution, in a conventional manner, or by reaction with the desired lower alkyl iodide in the presence of lithium carbonate, at room temperature.

The salt derivatives of the prostanoic acids of the present invention can be prepared by treating the corresponding free acids with about one molar equivalent of a pharmaceutically acceptable base per molar equivalent of free acid. Suitable pharmaceutically acceptable bases include, for example, sodium hydroxide, potassium hydroxide, magnesium hydroxide, calcium hydroxide, ammonium hydroxide, trimethylamine, triethylamine, tripropylamine, β-dimethylaminoethanol, β-diethylaminoethanol, arginine, lysine, caffeine, procaine and the like. Typically, the reaction is conducted in an aqueous solution, alone or in combination with an inert, water miscible organic solvent, at a temperature of about from 0° to 30°C, preferably at room temperature. Typical inert, water miscible organic solvents include methanol, ethanol, isopropanol, butanol, dioxane, and the like. When divalent metal salts are prepared, such as the calcium salts or magnesium salts, the free acid strting material is treated with at least one half molar equivalent of the pharmaceutically acceptable base.

The compounds used as starting materials in the process of the present invention can be prepared in accordance with the method described in our copending patent application Ser. No. 368,983 filed June 11, 1973 (PA-606) which is hereby incorporated by reference, as illustrated by the following reaction scheme:

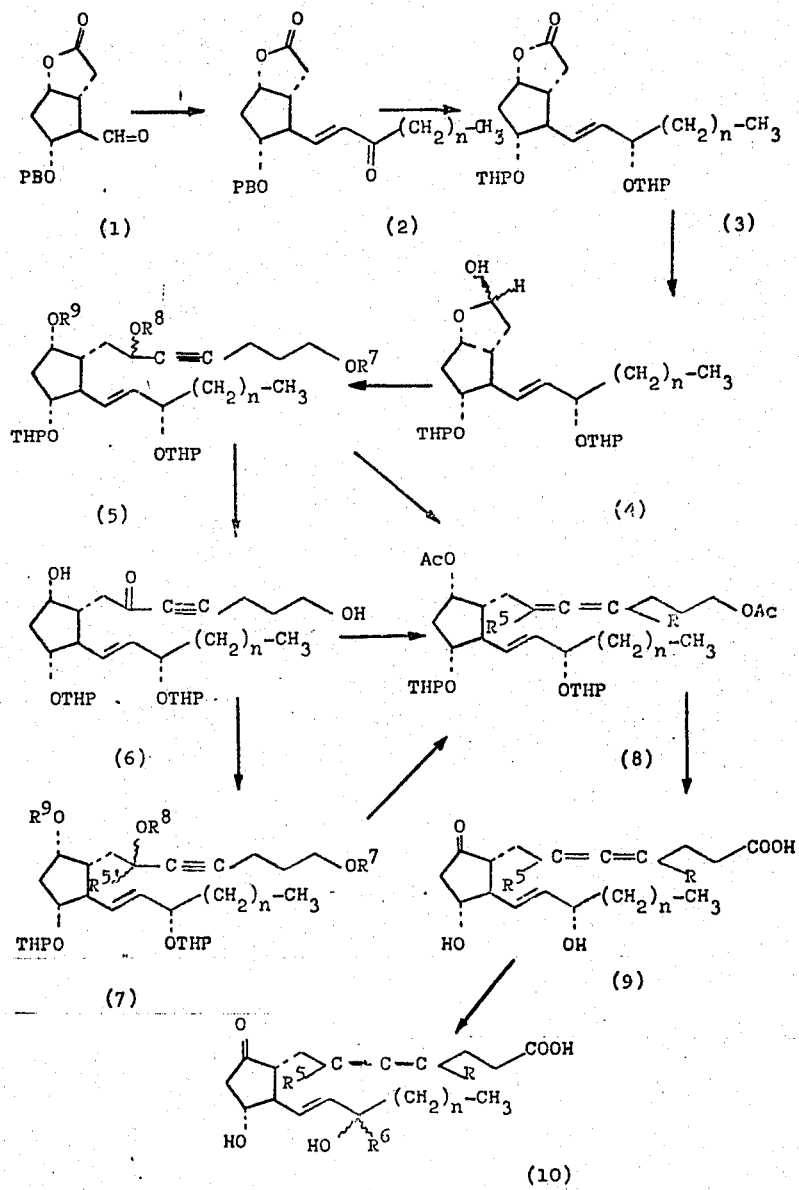

wherein R, $R^5$, $R^6$ and $n$ have the above-indicated meaning;

$R^{5'}$ is methyl, ethyl or propyl;

$R^7$, $R^8$ and $R^9$ are hydrogen or acetyl, PB is p-phenylbenzoyl;

THP is tetrahydropyranyl and Ac is acetyl.

This method comprises the condensation of (2'α-hydroxy-4'α-phenylbenzoyloxy-5'β-formylcyclopent-1'α-yl) acetic acid 1,2'-lactone or the 1'R-antimer thereof, which can be obtained as described by E. J. Corey et al., in *J. Am. Chem. Soc.* 93, 1491 (1971) and in the afore-mentioned patent application with the sodium anion of a dimethyl 2-oxo-n-alkylphosphonate of the formula

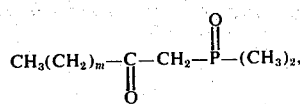

wherein $m$ is an integer of from 2 to 9, into to produce the corresponding [2'α-hydroxy-4'α-p-phenylbenzoyloxy-5'β-(3''-oxo-n-alk-1'''(t)-en-1-yl) cyclopent-1'α-yl)]-acetic acid 1,2'-lactone (2), or the 1'R-antimer thereof in which the 3''-oxo group is selectively reduced with zinc borohydride to a mixture of 3''α and 3''β-hydroxy compounds, separating the mixture into the individual isomers by thin layer chromatography. The p-phenylbenzoyloxy group is hydrolyzed in the 3''α-isomers and the dihydroxylated compound converted into the bistetrahydropyranyloxy derivative (3), e.g., [2'α-hydroxy-4'α-tetrahydropyranyloxy-5'β-(3''α-tetrahydropyranyloxyoct-1''(t)-en-1''-yl) cyclopent-1'α-yl)-acetic acid 1,2'-lactone, or the 1'R-antimer thereof, which is reduced to the corresponding lactol (4) by reaction with diisobutyl aluminum hydride in anhydrous toluene, at −60°C. The 1'R-antimeric or racemic lactol (4) is then treated with an excess of the dilithium salt of pent-4-yn-1-ol to yield the 8R-antimeric or racemic trihydroxyacetylenic compound of formula (.., $R^7$, $R^8$ and $R^9$ = H), which is converted into the corresponding triacetate (5, $R^7$, $R^8$ and $R^9$ = acetyl) by reaction with acetyl chloride in pyridine solution. Upon selective oxidation of the 8R-antimeric or racemic trihydroxyacetylenic compound (5, $R^7$, $R^8$ and $R^9$ = H) with manganese dioxide or 2,3-dichloro-5,6-dicyano-1,4-benzoquinone in a suitable inert organic solvent there is obtained the 8R-antimeric or racemic dihydroxy-keto-acetylenic compound (6), which is converted into the corresponding 6}-alkyl-6{-hydroxy derivative (7, $R^7$, $R^8$ and $R^9$= H) by reaction with 2 to 10 molar equivalents of methyl-, ethyl- or propyllithium or the corresponding alkylmagnesium halides. These compounds are then esterified via formation of the lithium salts followed by reaction with acetyl chloride in pyridine solution, to yield a mixture of the corresponding triacetate (7, $R^7$, $R^8$ and $R^9$ = acetyl) and the 1,9-diesterified compound, which are separated by chromatography.

By reaction of the 8R-antimeric or racemic triacetoxy acetylenic compounds (5, $R^7$, $R^8$ and $R^9$ = acetyl) with a lithium dialkylcopper in which the alkyl groups are the same, there are produced the 8R-antimeric or racemic allenic compounds substituted or unsubstituted at C-4 and unsubstituted at C-6 (8, R=H, Me, Et or Pr; $R^5$ = H), depending upon the reaction conditions used. Thus, when the reaction is conducted at temperatures of between about −50° to −78°C for about 3 to 7 hours, using 4 molar equivalents of the reagent, employing particularly lithium dimethylcopper as reagent, there is obtained the corresponding allenic compound unsubstituted at C-4 and C-6 (8, R and $R^5$ = H). When the reaction is effected at 0°C for the same reaction time, using only about one molar equivalent of the organocopper reagent there are obtained the 4-alkyl substituted allenes (8, R = Me, Et, Pr, $R^5$ = H). When the above-described reactions with a lithium dialkylcopper are effected upon the 6-alkyl triesters of formula (7, $R^7$, $R^8$ and $R^9$ = acetyl) there are obtained the corresponding 6-alkyl or 4,6-dialkylallenes (8, R = H, Me, Et, Pr; $R^5$ = Me, Et, Pr), depending upon the reaction conditions used.

Upon alkaline hydrolysis of the acyloxy groups in any of the 8R-antimeric or racemic allenic compounds of formula (8), oxidation with chromic acid and mild acid hydrolysis of the tetrahydropyranyloxy groups there are obtained the 8R-antimeric or racemic 9-keto-11α,15α-dihydroxyprosta-4,5,13-trans-trienoic acids (substituted or unsubstituted at C-4 and/or C-6) represented by formula (9), which are used as starting materials in the process object of the invention.

The 15-alkyl derivatives thereof (10) are obtained from 8R-antimeric or racemic compounds of formula (9), or the corresponding 15β-hydroxy isomers via esterification of the carboxylic acid function, protection of the 9-keto group as the oxime, oxidation of the hydroxyl group at C-15 with manganese dioxide or 2,3-dichloro-5,6-dicyano-1,4-benzoquinone, protection of the hydroxyl group as the trimethylsilylether (with concomitant reaction of the hydroxyimino group), treatment of the protected compound with an excess of a methyl-, ethyl- or propylmagnesium halide or an alkyllithium to yield the corresponding 15{-hydroxy, 15{-alkyl compounds, separation of the 15α-hydroxy-15β-alkyl and 15β-hydroxy-15α-alkyl isomers, hydrolysis of the protecting groups at C-9 and C-11 and final hydrolysis of the alkyl ester group, by enzymatic methods.

The compounds, esters and salts of the invention exhibit prostaglandin-like biological activities and thus are useful in the treatment of mammals where the use of prostaglandins are indicated. The compounds, esters and salts of the invention are bronchodilators and thus are useful in treating mammals for bronchial spasm or wherever strong bronchodilators are indicated. These compounds are also useful in controlling or palliating hypertension in mammals and further exhibit central nervous system depressant activity in mammals, and are useful as sedatives. In addition, the compounds are useful for inducing labor, in pregnancy, and for inducing menses to correct or reduce menstrual abnormalities.

The compounds and/or salts of the invention can be administered in a wide variety of dosage forms, either alone or in combination with other pharmaceutical compatible medicaments, in the form of pharmaceutical compositions suited for oral or parenteral administration or inhalation in the case of bronchodilators. The compounds are typically administered as pharmaceutical compositions consisting essentially of the compounds and/or salts, of the invention, and a pharmaceutical carrier. The pharmaceutical carrier can be either a solid material, liquid or aerosol, in which the compound and/or salt is dissolved, dispersed or suspended, and can optionally contain small amounts of preservatives and/or pH-buffering agents. Suitable preservatives which can be used include, for example, benzyl alcohol and the like. Suitable buffering agents include, for example, sodium acetate and pharmaceutical phosphate salts and the like.

The liquid compositions can, for example, be in the form of solutions, emulsions, suspensions, syrups or elixirs. The solid compositions can take the form of tablets, powders, capsules, pills or the like, preferably in unit dosage forms for simple administration or precise dosages. Suitable solid carriers include, for example, pharmaceutical grades of starch, lactose, sodium saccharin, talcum, sodium bisulfite and the like.

For inhalation administration, the compounds and/or salts can, for example, be administered as an aerosol comprising the compounds or salts in an inert propellant together with a cosolvent e.g., ethanol, together with optional preservatives and buffering agents. Additional general information concerning the inhalation administration of aerosols can be had by reference to U.S. Pat. Nos. 2,868,691 and 3,095,355.

The compounds of this invention are typically administered in dosages of about from 0.01 to 10 mg. per Kg. of body weight. The precise effective dosage will, of course, vary depending upon the mode of administration, condition being treated and host.

The following Examples illustrate the invention, but are not intended to limit its scope. The abbreviation t.l.c. refers to thin-layer chromatography and all mixture ratios used with regard to liquids refer to volume ratios. Also, where necessary, Examples are repeated to provide sufficient starting material for subsequent Examples.

PREPARATION 1

A. A solution of 100 g. of dimethyl methylphosphonate in 670 ml. of anhydrous tetrahydrofuran is cooled to −78°C. under an argon atmosphere. To the cold solution are added dropwise under stirring and under argon atmosphere, 495 ml. of a 0.1M solution of n-butyllithium in tetrahydrofuran, maintaining the temperature at −70°C. When the addition is complete the reaction mixture is maintained under the same conditions for 10 additional minutes, a solution of 58 ml. of methyl caproate dissolved in 187 ml. of tetrahydrofuran is then carefully added, maintaining the temperature at −78°C. The reaction mixture is stirred at −78°C. for 2 hours followed by stirring for 4 hours at room temperature. The excess base is neutralized with acetic acid and the solvent is evaporated under high vacuo. The residue is dissolved in ether-water (1:1, 950 ml. each), the ethereal phase is separated, washed with water and dried over magnesium sulfate. The ether is evaporated and the residue is purified by vacuum distillation, thus obtaining the pure dimethyl 2-oxoheptylphosphonate.

In a similar manner but using methyl n-butanoate, methyl n-pentanoate, ethyl n-heptanoate, ethyl n-octanoate and methyl n-undecanoate in place of methyl caproate, there are respectively obtained: dimethyl 2-oxopentylphosphonate, dimethyl 2-oxohexylphosphonate, dimethyl 2-oxo-octylphosphonate, dimethyl 2-oxononylphosphonate and dimethyl 2-oxododecylphosphonate.

B. To a suspension of 1.55 g. of sodium hydride (previously washed with pentane, under argon) in 355 ml. of dimethoxyethane freshly distilled from lithium aluminum hydride is added, under stirring and under an atmosphere of argon, a solution of 7.1 g. of dimethyl 2-oxoheptylphosphonate in 150ml. of dimethoxyethane. The reaction mixture is stirred for 30 minutes at room temperature and 10 g. of 1′R-(2′α-hydroxy-4′α-p-phenylbenzoyloxy-5′β-formyl-cyclopent-1′α-yl)-acetic acid 1,2′-lactone obtained as described by E. J. Corey et al in *J. Am. Chem. Soc.* 93, 1491(1971) are added. The reaction mixture is stirred at room temperature for 2 hours further, it is then carefully neutralized with acetic acid (to pH 7) and evaporated to dryness under reduced pressure at a temperature below 30°C. The solid residue is purified by chromatography on Florisil, using methylene chloride as eluant, to obtain 1′R-[2′α-hydroxy-4′α-phenylbenzoyloxy-5′β-(3″-oxo-oct-1″(t)-en-1″-yl) cyclopent-1′α-yl]-acetic acid 1,2′-lactone [1′ R-antimer of (2),$n = 4$] and a small amount of dimethyl 2-oxoheptylphosphonate.

Likewise but using dimethyl 2-oxopentylphosphonate, dimethyl-2-oxohexylphosphonate, dimethyl 2-oxooctylphosphonate, dimethyl 2-oxononylphosphonate and dimethyl 2-oxododecylphosphonate in place of dimethyl 2-oxoheptylphosphonate, there are produced:

1′R-[2′α-hydroxy-4′α-p-phenylbenzoyloxy-5′β-(3″-oxohex-1″(t)-en-1″-yl) cyclopent-1′α-yl]-acetic acid 1,2′-lactone, 1′R-[2′α-hydroxy-4′α-p-phenylbenzoyloxy-5′β-(3″-oxohept-1″(t)-en-1″-yl) cyclopent-1′α-yl]-acetic acid 1,2′-lactone, 1′R-[2′α-hydroxy-4′α-p-phenylbenzoyloxy-5′β-(3″-oxonon-1″ (t)-en-1″-yl) cyclopent-1′α-yl]-acetic acid 1,2′-lactone, 1′R-[2′α-hydroxy-4′α-p-phenylbenzoyloxy-5′β-(3″-oxodec-1″(t)-en-1″-yl) cyclopent-1′α-yl]-acetic acid 1,2′-lactone and 1′R-[2′α-hydroxy-4′α-p-phenylbenzoyloxy-5′β-(3″-oxotridec-1″(t)-en-1″-yl) cyclopent-1′α-yl]-acetic acid 1,2′-lactone.

In a similar manner but using (2′α-hydroxy-4′α-p-phenylbenzoyloxy-5′β-formylcyclopent-1′α-yl)-acetic acid 1,2′-lactone as starting material there are obtained the corresponding racemic compounds.

PREPARATION 2

To a stirred solution of 5.34 g. of 1′R-[2′α-hydroxy-4′α-p-phenylbenzoyloxy-5′β-(3″-oxo-oct-1″(t)-en-1″-yl) cyclopent-1′α-yl]-acetic acid 1,2′-lactone in 36 ml. of dimethoxyethane freshly distilled from lithium aluminum hydride are added 9 ml. of zinc borohydride reagent in anhydrous dimethoxyethane. The reaction mixture is stirred for an additional hour at room temperature, and treated with a saturated solution of sodium bitartrate until the evolution of gas ceases. It is then diluted with methylene chloride, dried over magnesium sulfate and evaporated to dryness under vacuo at a temperature below 30°C. to yield 1′R-[2′α-hydroxy-4′α-p-phenylbenzoyloxy-5′β-(3″α-hydroxyoct-1″(t)-en-1″-yl) cyclopent-1′α-yl]-acetic acid 1,2′-lactone in mixture with the 3″β-hydroxy isomer.

The oily mixture is separated into the individual isomers by t.l.c. using a mixture of benzene-methylisobutyl ketone (2:1) as eluant.

Similarly, the remaining 3″-oxo 1′R-compounds obtained in Preparation 1 are converted into the respective 3″-hydroxy compounds, namely:

1′R-[2′α-hydroxy-4′α-p-phenylbenzoyloxy-5′β-(3″α-hydroxyhex-1″(t)-en-1″-yl) cyclopent-1′αyl]-acetic acid 1,2′-lactone, 1′R-[2′α-hydroxy-4′α-p-phenylbenzoyloxy-5′β-(3″α-hydroxyhept-1″(t)-en-1″-yl) cyclopent-1′α-yl]-acetic acid 1,2′-lactone, 1′R-[2′α-hydroxy-4′α-p-phenylbenzoyloxy-5′β-(3″α-hydroxynon-1″(t)-en-1″-yl) cyclopent-1′α-yl]-acetic acid 1,2′-lactone, 1′R-[2′α-hydroxy-4′α-p-phenylbenzoyloxy-5′β-(3″α-hydroxydec-1″(t)-en-1″-yl) cyclopent-1″α-yl]-acetic acid 1,2′-lactone and 1′R-[2′α-hydroxy-4′α-p-phenylbenzoyloxy-5′β-(3″α-hydroxytridec-1″(t)-en-1″αcyclopent-1′α-yl]-acetic acid 1,2′-lactone, in mixture with the corresponding 3″β-hydroxy isomers, which are separated by thin layer chromatography.

Likewise starting from the corresponding racemic 3″-oxo compounds there are produced the respective racemic 3″-hydroxylated derivatives.

The zinc borohydride reagent is prepared from 0.025 mol of fused zinc chloride, 0.050 mol of sodium borohydride and 50 ml. of dimethoxyethane, stirring the mixture for 16 hours and filtering the insoluble material under argon atmosphere.

PREPARATION 3

A. A solution of 3.7 g. of 1′R-[2′α-hydroxy-4′α-p-phenylbenzoyloxy-5′β-(3″α-hydroxyoct-1″(t)-en-1″-yl) cyclopent-1′α-yl]-acetic acid 1,2′-lactone in 37 ml. of anhydrous methanol is treated with 1.14 g. of anhydrous potassium carbonate, and the reaction mixture stirred for 2½ hours at room temperature. It is then cooled to 0°C. and adjusted with 10N aqueous hydrochloric acid until a pH of 2–3 is obtained. Ethyl acetate is added and the organic solution washed with saturated sodium bicarbonate solution and saturated sodium potassium bitartrate solution, dried over magnesium sulfate and evaporated to dryness under vacuo. The residue is purified by filtration through a Florisil column (130 g.). The fractions eluted with methylene chloride-ethyl acetate give methyl-p-biphenyl carboxylate and the fractions eluted with ethyl acetate yield 1′R-[2′α,4′α-dihydroxy-5′β-(3″α-hydroxyoct-1′″(t)-en-1″-yl) cyclopent-1′α-yl]-acetic acid 1,2′-lactone.

B. To a solution of 2.3 g of [2'α,4'α-dihydroxy-5'β-(3''α-hydroxyoct-1''(t)-en-1''-yl) cyclopent-1'α-yl]-acetic acid 1,2'-lactone in 23 ml. of methylene chloride are added 2.3 ml. of freshly distilled dihydropyran and 23 mg. of anhydrous p-toluenesulfonic acid. The reaction mixture is stirred for 15 minutes at room temperature, a few drops of pyridine are added and diluted with ether. The ethereal solution is washed with 100 ml. of 50% aqueous sodium chloride solution and then with saturated sodium solution. The organic phase is separated, dried over magnesium sulfate and evaporated to dryness under reduced pressure, at approximately 0°C., thus yielding 1'R-[2'α-hydroxy-4'α-tetrahydropyranyloxy-5'β-(3''α-tetrahydropyranyloxyoct-1''(t)-en-1''-yl) cyclopent-1'α-yl]-acetic acid 1,2'-lactone, as an oil [1'R-antimer of (3), $n = 4$].

By the same method, from the corresponding 1'R-antimeric 4'α-p-phenylbenzoyloxy compounds obtained as described in Preparation 2, there are produced as final products:

1'R-[2'α-hydroxy-4'α-tetrahydropyranyloxy-5'β-(3''α-tetrahydropyranyloxyhex-1''(t)-en-1''-yl) cyclopent-1'α-yl]-acetic acid 1,2'-lactone.

1'R-[2'α-hydroxy-4'α-tetrahydropyranyloxy-5'β-(3''α-tetrahydropyranyloxyhept-1''(t)-en-1''-yl) cyclopent-1'α-yl]-acetic acid 1,2'-lactone, 1'R-[2'α-hydroxy-4'α-tetrahydropyranyloxy-5'β-(3''α-tetrahydropyranyloxynon-1''(t)-en-1''-yl) cyclopent-1'α-yl]-acetic acid 1,2'-lactone.

1'R-[2'α-hydroxy-4'α-tetrahydropyranyloxy-5'β-(3''α-tetrahydropyranyloxydec-1''(t)-en-1''-yl) cyclopent-1'α-yl]-acetic acid 1,2'-lactone and 1'R-[2'α-hydroxy-4'α-tetrahydropyranyloxy-5'β-(3''α-tetrahydropyranyloxytridec-1''(t)-en-1''-yl) cyclopent-1'α-yl]-acetic acid 1,2'-lactone.

Similarly, starting from the corresponding racemic 4'α-p-phenylbenzoyloxy compounds, there are obtained the corresponding racemates.

PREPARATION 4

One gram of 1'R-[2'α-hydroxy-4'α-tetrahydropyranyloxy-5'β-(3''α-tetrahydropyranyloxyoct-1''(t)-en-1''-yl) cyclopent-1'α-yl]-acetic acid 1,2'-lactone is dissolved in 20 ml. of anhydrous toluene. The solution is cooled to −60°C. and to the cold solution is added 3.43 ml. of a mixture of 1 ml. of diisobutyl aluminum hydride and 3 ml. of anhydrous toluene, stirring the reaction mixture for 15 minutes at −60°C. It is then diluted with methanol until the evolution of gas ceases, the mixture is stirred for 15 minutes further at room temperature and diluted with ether. The organic phase is then separated, washed with saturated sodium chloride solution, dried over magnesium sulfate and evaporated to dryness at about 0°C. to produce 1'R-[2'α-hydroxy-4'α-tetrahydropyranyloxy-5'β-[3''α-tetrahydropyranyloxyoct-1''(t)-en-1''-yl) cyclopent-1'α-yl]-acetaldehyde 1,2'-hemiacetal [1'R-antimer of (4) $n = 4$].

Similarly, the remaining compounds obtained in Preparation 3 are converted into the respective lactols, namely:

1'R-[2'α-hydroxy-4'α-tetrahydropyranyloxy-5'β-(3''α-tetrahydropyranyloxyhex-1''(t)-en-1''-yl) cyclopent-1'α-yl] acetaldehyde 1,2'-hemiacetal, 1'R-[2'α-hydroxy-4'α-tetrahydropyranyloxy-5'β-(3''α-tetrahydropyranyloxyhept-1''(t)-en-1''-yl) cyclopent-1'α-yl] acetaldehyde 1,2'-hemiacetal.

1'R-[2'α-hydroxy-4'α-tetrahydropyranyloxy-5'β-(3''α-tetrahydropyranyloxynon-1''(t)-en-1''-yl) cyclopent-1'α-yl] acetaldehyde 1,2'-hemiacetal, 1'R-[2'α-hydroxy-4'α-tetrahydropyranyloxy-5'β-(3''α-tetrahydropyranyloxydec-1''(t)-en-1''-yl) cyclopent-1'α-yl]-acetaldehyde 1,2'-hemiacetal and 1'R-[2'α-hydroxy-4'α-tetrahydropyranyloxy-5'β-(3''α-tetrahydropyranyloxytridec-1''(t)-en-1''-yl) cyclopent-1'α-yl]-acetaldehyde 1,2'-hemiacetal, as well as the corresponding racemates.

Preparation 5.

A mixture of 21.4 g. of pent-4-yn-1-ol and 1.25 l. of anhydrous ether is cooled under an argon atmosphere to −70°C. in a dry ice-acetone bath. To the stirred cold mixture is added dropwise 262 ml. of 2M methyllithium in ether.

After addition of this reagent, the reaction mixture is allowed to attain room temperature, stirring for 18 hours further. A solution of 3.8 g. of 1'R-[2'α-hydroxy-4'α-tetrahydropyranyloxy-5'β-(3''α-tetrahydropyranyloxyoct-1''(t)-en-1''-yl) cyclopent-1'α-yl]-acetaldehyde 1,2'-hemiacetal in 50 ml. of anhydrous ether is added, and the mixture is stirred for 6 hours at room temperature. It is then poured into ice water and extracted several times with ether. The combined organic extracts are washed with saturated sodium chloride solution, dried over magnesium sulfate and evaporated to dryness under reduced pressure, at a temperature not higher than 20°C. The residue is purified by chromatography on Florisil. The fractions eluted with ethyl acetate-methanol (90:10) give 8R-1,6{,9α-trihydroxy-11α,15α-bistetrahydropyranyloxyprost-4-yn-13-trans-ene, [8R-antimer of (5), $R^7$, $R^8$ and $R^9 = H$; $n = 4$].

The 6α and 6β-hydroxy isomers can be separated by t.l.c. on silica gel, using a mixture of methylene chloride-ether (1:1) as eluant.

PREPARATION 6

A mixture of 3 g. of 8R-1,6{,9α-trihydroxy-11α,15α-bistetrahydropyranyloxyprost-4-yn-13-trans-ene, 20 ml. of pyridine and 2 ml. of acetyl chloride is stirred at room temperature for 6 hours. It is then poured into water and extracted with ether. The organic extract is washed with saturated sodium chloride solution, dried over magnesium sulfate and evaporated to dryness under vacuo to yield 8R-1,6{,9α-triacetoxy-11α,15α-bistetrahydropyranyloxyprost-4-yn-13-trans-ene which can be purified by filtration through Florisil [8R-antimer of (5), $R^7$, $R^8$ and $R^9 = $ acetyl; $n = 4$].

PREPARATION 7

A stirred suspension of 2.9 g. of cuprous iodide in 75 ml. of anhydrous ether is cooled to about −10°C, under an atmosphere of argon, and treated with two molar equivalents of a 2M solution of methyllithium in ether. The resultant colorless solution is cooled to −75°C. in a dry ice-acetone bath, a solution of 2.4 g. of 8R-1,6{,9α-triacetoxy-11α,15α-bistetrahydropyranyloxyprost-4-yn-13-trans-ene in 75 ml. of anhydrous ether is then added and the reaction mixture stirred at −75°C. for 5 hours. The temperature of the mixture is raised to −10°C., saturated ammonium chloride solution is added, and the mixture is stirred, for one hour and extracted with ether. The organic extract is washed with saturated sodium chloride solution, dried over magnesium sulfate and evaporated to dryness under reduced pressure. The residue is purified by chromatography on Florisil. The fractions eluted with methylene chloride-ether (80:20) afford the pure 8R-1,9α-diacetoxy-11α,15α-bistetrahydropyranyloxyprosta-4,5,13-trans-triene [ 8R-antimer of (8), R and $R^5$ = H; $n = 4$].

PREPARATION 8

A mixture of 1.1 g. of 8R-1,9α-diacetoxy-11α,15α-bistetrahydropyranyloxyprosta-4,5,13-trans-triene, 550 mg. of anhydrous potassium carbonate and 20 ml. of anhydrous methanol is stirred at room temperature for 18 hours, under an argon atmosphere. The solvent is then eliminated under reduced pressure, water is added and the product extracted with ether. The ether extract is washed with saturated sodium chloride solution, dried over magnesium sulfate and evaporated to dryness under vacuo, thus yielding 8R-1,9α-dihydroxy-11α,15α-bistetrahydropyranyloxyprosta-4,5,13-trans-triene.

PREPARATION 9

A solution of 2 g. of 8R-1,9α-dihydroxy-11α,15α-bistetrahydropyranyloxyprosta-4,5,13-trans-triene in 60 ml. of acetone is cooled to −10°C. and treated under an atmosphere of nitrogen and with stirring, with 4 ml. of an 8N solution of chromic acid (prepared by mixing 26 g. of chromium trioxide with 23 ml. of concentrated sulfuric acid and diluting with water to 100 ml.). The reaction mixture is stirred for 90 minutes further at −10°C., a few drops of isopropanol are then added to destroy the excess reagent, and the mixture diluted with ethyl acetate. The solution is immediately washed three times with sodium chloride solution, dried over magnesium sulfate and evaporated to dryness under reduced pressure. To the oily residue is added 16 ml. of a mixture of acetic acid-water (65:35), and the reaction mixture is stirred at room temperature for 18 hours, it is then evaporated to dryness under vacuo and the residue purified by t.l.c. using ethyl acetate as eluant, to give the pure 8R-9-keto-11α,15α-dihydroxyprosta-4,5,13-trans-trienoic acid [8R-antimer of (9), R and $R^5$ = H; $n = 4$].

PREPARATION 10

Preparations 5 to 9 are repeated using as starting materials:

1′R-[2′α-hydroxy-4′α-tetrahydropyranyloxy-5′β-(3″α-tetrahydropyranyloxyhex-1‴(t)-en-1‴-yl) cyclopent-1′α-yl)]-acetaldehyde 1,2′-hemiacetal, 1′R-[2′α-hydroxy-4′α-tetrahydropyranyloxy-5′β-(3″α-tetrahydropyranyloxyhept-1‴(t)-en-1‴-yl) cyclopent-1′α-yl]-acetaldehyde 1,2′-hemiacetal, 1′R-[2′α-hydroxy-4′α-tetrahydropyranyloxy-5′β-(3″α-tetrahydropyranyloxynon-1‴(t)-en-1‴-yl) cyclopent-1′α-yl]-acetaldehyde 1,2′-hemiacetal, 1′R-[2′α-hydroxy-4′α-tetrahydropyranyloxy-5′β-(3″α-tetrahydropyranyloxydec-1‴(t)-en-1‴-yl) cyclopent-1′α-yl]-acetaldehyde 1,2′-hemiacetal and 1′R-[2′α-hydroxy-4′α-tetrahydropyranyloxy-5′β-(3″α-tetrahydropyranyloxytridec-1‴(t)-en-1‴-yl) cyclopent-1′α-yl]-acetaldehyde 1,2′-hemiacetal, to yield as final products, respectively:

8R-9-keto-11α,15α-dihydroxy-20-bisnorprosta-4,5,13-trans-trienoic acid, 8R-9-keto-11α,15α-dihydroxy-20-norprosta-4,5,13-trans-trienoic acid, 8R-9-keto-11α,15α-dihydroxy-20-methylprosta-4,5,13-trans-trienoic acid, 8R-9-keto-11α,15α-dihydroxy-20-ethylprosta-4,5,13-trans-trienoic acid and 8R-9-keto-11α,15α-dihydroxy-20-pentylprosta-4,5,13-trans-trienoic acid.

Similarly, starting from the racemic compounds corresponding to the above-mentioned 1′R-antimeric lactols there are produced the respective racemic prostatrienoic acid derivatives, e.g. 9-keto-11α,15α-dihydroxyprosta-4,5,13-trans-trienoic acid and 9-keto-11α,15α-dihydroxy-20-ethylprosta-4,5,13-trans-trienoic acid.

PREPARATION 11

A. To a vigorously stirred suspension of 10.4 g. of cuprous iodide in 200 ml. of diethyl ether, cooled to 0°C., is added dropwise a 2M solution of methyllithium in ether, under argon atmosphere, until a colorless solution of lithium dimethylcopper reagent is obtained.

In a similar manner but using ethyllithium and propyllithium instead of methyllithium, the lithium diethylcopper and lithium di-n-propylcopper reagents are prepared.

B. A solution of 500 mg. of 8R-1,6,9α-triacetoxy-11α,15α-bistetrahydropyranyloxyprost-4-yn-13-trans-ene in 15 ml. of anhydrous ether is cooled to 0°C. and treated, under argon atmosphere, with one molar equivalent of lithium dimethylcopper (prepared as described in Part A). The reaction mixture is stirred for 5 hours at 0°C., saturated ammonium chloride solution is added, and the mixture is stirred for 1 hour and extracted with ether. The organic extract is washed with saturated sodium chloride solution, dried over magnesium sulfate and evaporated to dryness under reduced pressure. The residue is purified by chromatography on Florisil. The fractions eluted with methylene chloride-ether (80:20) afford the pure 8R-1,9α-diacetoxy-11α,15α-bistetrahydropyranyloxy-4-methylprosta-4,5,13-trans-triene [8R-antimer of (8), R = Me; $R^5$ = H; $n = 4$].

Similarly, but using one molar equivalent of lithium diethylcopper and lithium dipropylcopper in lieu of lithium dimethylcopper there are respectively obtained 8R-1,9α-diacetoxy-11α,15α-bistetrahydropyranyloxy-4-ethylprosta-4,5,13-trans-triene and 8R-1,9α-diacetoxy-11α,15α-bistetrahydropyranyloxy-4-propyl-prosta-4,5,13-trans-triene.

Upon saponification of the acetoxy functions in the above compounds followed by oxidation and hydrolysis of the tetrahydropyranyloxy groups, in accordance with the methods of Preparations 8 and 9, there are obtained as final products, respectively:

8R-4-methyl-9-keto-11α,15α-dihydroxyprosta-4,5,13-trans-trienoic acid [8R-antimer of (9), R = Me; $R^5$ = H; $n = 4$], 8R-4-ethyl-9-keto-11α,15α-dihydroxyprosta-4,5,13-trans-trienoic acid, and 8R-4-propyl-9-keto-11α,15α-dihydroxyprosta-4,5,13-trans-trienoic acid.

In a similar manner, starting from 8R-1,6,9α-triacetoxy-11α,15α-bistetrahydropyranyloxy-20-bisnorprost-4-yn-13-trans-ene, 8R-1,6,9α-triacetoxy-11α,15α-bistetrahydropyranyloxy-20-norprost-4-yn-13-trans-ene, 8R-1,6,9α-triacetoxy-11α,15α-bistetrahydropyranyloxy-20-methylprost-4-yn-13-trans-ene, 8R-1,6¦,9α-triacetoxy-11α,15α-bistetrahydropyranyloxy-20-ethylprost-4-yn-13-trans-ene and 8R-1,6¦,9α-triacetoxy-11α,15α-bistetrahydropyranyloxy-20-pentylprost-4-yn-13-trans-ene, using lithium dimethylcopper as reagent, there are obtained as final products, respectively:

8R-4-methyl-9-keto-11α,15α-dihydroxy-20-bisnorprosta-4,5,13-trans-trienoic acid, 8R-4-methyl-9-keto-11α,15α-dihydroxy-20-norprosta-4,5,13-trans-trienoic acid, 8R-4,20-dimethyl-9-keto-11α,15α-dihydroxyprosta-4,5,13-trans-trienoic acid, 8R-4-methyl-9-keto-11α,15α-dihydroxy-20-ethylprosta-4,5,13-trans-trienoic acid and 8R-4-methyl-9-keto-11α,15α-dihydroxy-20-pentylprosta-4,5,13-trans-trienoic acid.

Similarly, starting from the racemic compounds corresponding to the above mentioned 8R-antimeric prost-4-yn-13-trans-enes mentioned above, there are produced the respective racemic 4-methyl-prostatrienoic acid derivatives, e.g., 4-methyl-9-keto-11α,15α-dihydroxyprosta-4,5,13-trans-trienoic acid, 4-methyl-9-keto-11α,15α-dihydroxy-20-ethylprosta-4,5,13-trans-trienoic acid, and 4-methyl-9-keto-11α,15α-dihydroxy-20-bisnorprosta-4,5,13-trans-trienoic acid.

PREPARATION 12

A. To a solution of 2 g. of 8R-1,6¦,9α-trihydroxy-11α,15α-bistetrahydropyranyloxyprost-4-yn-13-trans-ene in 60 ml. of anhydrous tetrahydrofuran is added 4.6 g. of activated manganese dioxide, and the reaction mixture is stirred for 90 minutes at room temperature; the manganese dioxide is filtered off and washed with acetone and the combined filtrates are evaporated to dryness under vacuo. The residue is redissolved in 60 ml. of anhydrous tetrahydrofuran, 4.6 g. of manganese dioxide are then added and the mixture stirred under the same conditions for 90 minutes further. The manganese dioxide is separated by filtration and washed with hot acetone. The conbined organic filtrates are evaporated to dryness under reduced pressure, and the residue is purified by thin layer chromatography, using a 1:1 methylene chloride-diethyl ether mixture containing 0.4% of methanol as eluant, to obtain 8R-1,9α-dihydroxy-6-keto-11α,15α-bistetrahydropyranyloxyprost-4-yn-13-trans-ene [8R-antimer of (6), $n = 4$], in pure form.

B. To a stirred solution of 1.1 g. of 8R-1,9α-dihydroxy-6-keto-11α,15α-bistetrahydropyranyloxyprost-4-yn-13-trans-ene in 200 ml. of anhydrous diethyl ether, there is added dropwise, at room temperature and under argon atmosphere, 3.84 ml. of a 2.2M solution of methyllithium in ether (4 molar equivalents). The reaction mixture is maintained at room temperature for 1 hour and then poured into a saturated aqueous ammonium chloride solution. The organic phase is separated and the aqueous phase extracted with ether. The combined organic extracts are washed with saturated aqueous sodium chloride solution, dried over magnesium sulfate and evaporated to dryness under reduced pressure. The residue is purified twice by thin layer chromatography, using a (49:49:2) methylene chloride-diethyl ether-methanol mixture as eluant for the first run, and then a (60:39:1) mixture of the same solvents for the second chromatography, to obtain 8R-6¦-methyl-1,6¦,9α -trihydroxy-11α,15α-bistetrahydropyranyloxyprost-4-yn-13-trans-ene pure form [8R-antimer of (7), $R^{5'} = Me$; $R^7$, $R^8$ and $R^9 = H$; $n = 4$].

C. To a solution of 1 g. 8R-6¦-methyl-1,6¦,9α-trihydroxy-11α,15α-bistetrahydropyranyloxyprost-4-yn-13-trans-ene in 100 ml. of anhydrous ether there is added 5 ml. of a 2.2M solution of methyllithium in ether, and the reaction mixture is stirred at room temperature for 3½ hours. The reaction mixture is then cooled to 0°C in an ice bath and treated dropwise under stirring with 3.1 ml. of acetyl chloride and thereafter 6.1 ml. of pyridine are added. The resultant mixture is then stirred at room temperature for 18 hours, water is then added and the product extracted with ether. The organic extracts are washed 3 times with saturated aqueous sodium chloride solution, dried over magnesium sulfate and evaporated to dryness under vacuo. The residue is purified by t.l.c. using methylene chloride-ether (80:20), thus obtaining 8R-6¦-methyl-1,6¦,9α-triacetoxy-11α,15α-bistetrahydropyranyloxyprost-4-yn-13-trans-ene [8R-antimer of (7), $R^{5'} = Me$; $R^7$, $R^8$ and $R^9 = $ acetyl; $n = 4$] and 8R-6¦-methyl-1,9α-diacetoxy-6¦-hydroxy-11α,15α-bistetrahydropyranyloxyprost-4-yn-13-trans-ene in pure form.

D. A stirred suspension of 1.17 g. of cuprous iodide in 20 ml. of anhydrous ether is cooled to about −10°C under an atmosphere of argon, and treated with 2 molar equivalents of a 2M solution of methyllithium in ether. The resultant colorless solution is cooled to −70°C in a dry ice-acetone bath, a solution of 1 g. of 8R-6¦-methyl-1,6¦,9α-triacetoxy-11α,15α-bistetrahydropyranyloxyprost-4-yn-13-trans-ene in 30 ml. of anhydrous ether is then added and the reaction mixture stirred at −70°C for 5 hours. The temperature of the mixture is raised to −10°C, saturated ammonium chloride solution is added, and the mixture is stirred for 1 hour and extracted with ether. The organic extract is washed with saturated sodium chloride solution, dried over magnesium sulfate and evaporated to dryness under reduced pressure, to afford 8R-6-methyl-1,9α-diacetoxy-11α,15α-bistetrahydropyranyloxyprosta-4,5,13-trans-triene [8R-antimer of (8), $R = H$; $R^5 = Me$; $n = 4$].

E. A mixture of 550 mg. of 8R-6-methyl-1,9α-diacetoxy-11α,15α-bistetrahydropyranyloxyprosta-4.5,13-trans-triene, 250 mg. of anhydrous potassium carbonate and 10 ml. of anhydrous methanol is stirred at room temperature for 18 hours, under an argon atmosphere. The solvent is then eliminated under reduced pressure, water is added and the product extracted with ether. The ether extract is washed with saturated sodium chloride solution, dried over magnesium sulfate and evaporated to dryness under reduced pressure to afford 8R-6-methyl-1,9α-dihydroxy-11α,15α-bistetrahydropyranyloxyprosta-4,5,13-trans-triene.

Upon oxidation of the latter compound with 8N chromic acid followed by hydrolysis of the tetrahydropyranyloxy functions with aqueous 65% acetic acid, in accordance with the methods of Preparation 9, there is produced 8R-6-methyl-9-keto-11α,15α-dihydroxyprosta-4,5,13-trans-trienoic acid [8R-antimer of (9), $R = H$; $R^5 = Me$; $n = 4$].

Likewise, by repeating the procedures described in this Preparation starting from:

8R-1,6¦,9α-trihydroxy-11α,15α-bistetrahydropyranyloxy-20-bisnorprost-4-yn-13-trans-ene, 8R-1,6¦,9α-trihydroxy-11α,15α-bistetrahydropyranyloxy-20-norprost-4-yn-13-trans-ene, 8R-1,6ξ,9α-trihydroxy-11α,15α-bistetrahydropyranyloxy-20-methylprost-4-yn-13-trans-ene, 8R-1,6ξ,9α-trihydroxy-11α,15α-bistetrahydropyranyloxy-20-ethylprost-4-yn-13-trans-ene, 8R-1,6ξ,9α-trihydroxy-11α,15α-bistetrahydropyranyloxy-20-pentylprost-4-yn-13-trans-ene, 1,6ξ,9α-trihydroxy-11α,15α-bistetrahydropyranyloxyprost-4-yn-13-trans-ene, 1,6ξ,9α-trihydroxy-11α,15α-bistetrahydropyranyloxy-20-ethylprost-4-yn-13-trans-ene and 1,6ξ,9α-trihydroxy-11α,15α-bistetrahydropyranyloxy-20-norprost-4-yn-13-trans-ene, there are obtained as final products:

8R-6-methyl-9-keto-11α,15α-dihydroxy-20-bisnorprosta-4,5,13-trans-trienoic acid, 8R-6-methyl-9-keto-11α,15α-dihydroxy-20-norprosta-4,5,13-trans-trienoic acid, 8R-6,20-dimethyl-9-keto-11α,15α-dihydroxyprosta-4,5,13-trans-trienoic acid, 8R-6-methyl-9-keto-11α,15α-dihydroxy-20-ethylprosta-4,5,13-trans-trienoic acid, 8R-6-methyl-9-keto-11α,15α-dihydroxy-20-pentylprosta-4,5,13-trans-trienoic acid, 6-methyl-9-keto-11α,15α-dihydroxyprosta-4,5,13-trans-trienoic acid, 6-methyl-9-keto-11α,15α-dihydroxy-20-ethylprosta-4,5,13-trans-trienoic acid and 6-methyl-9-keto-11α,15α-dihydroxy-20-norprosta-4,5,13-trans-trienoic acid, respectively.

In a similar manner but using ethyllithium and propyllithium in place of methyllithium in part C of this Preparation, the corresponding 6-ethyl and 6-propyl prostatrienoic acid compounds are produced.

PREPARATION 13

A solution of 100 mg. of 8R-6ξ-methyl-1,6ξ,9α-triacetoxy-11α,15α-bistetrahydropyranyloxyprost-4-yn-13-trans-ene in 3 ml. of anhydrous ether is cooled to 0°C and treated, under argon atmosphere, with one molar equivalent of lithium dimethylcopper, (prepared as described in part A of Preparation 11). The reaction mixture is stirred for 5 hours at 0°C, saturated ammonium chloride solution is added, and the mixture is stirred for 1 hour and extracted with ether. The organic extract is washed with saturated sodium chloride solution, dried over magnesium sulfate and evaporated to dryness under reduced pressure. The residue is purified by chromatography of Florisil. The fractions eluted with methylene chloride-ether (80:20) afford the pure 8R-4,6-dimethyl-1,9α-diacetoxy-11α,15α-bistetrahydropyranyloxyprosta-4,5,13-trans-triene [8R-antimer of (8), R and R⁵ = Me; $n = 4$].

Upon saponification of the acetoxy functions in the latter compound, followed by oxidation and hydrolysis of the tetrahydropyranyloxy groups, in accordance with the methods of Preparations 8 and 9, there is produced as final product 8R-4,6-dimethyl-9-keto-11α,15α-dihydroxyprosta-4,5,13-trans-trienoic acid [8R-antimer of (9), R and R⁵ = Me; $n = 4$].

In a similar manner but using lithium diethylcopper and lithium dipropylcopper in lieu of lithium dimethylcopper there are obtained as final products 8R-4-ethyl-6-methyl-9-keto-11α,15α-dihydroxyprosta-4,5,13-trans-trienoic acid and 8R-4-propyl-6-methyl-9-keto-11α,15α-dihydroxyprosta-4,5,13-transtrienoic acid, respectively.

Likewise, starting from 6ξ-methyl-1,6ξ,9α-triacetoxy-11α,15α-bistetrahydropyranyloxyprosta-4-yn-13-trans-ene, using in the first step the appropriate lithium dialkylcopper reagent, there are produced:

4,6-dimethyl-9-keto-11α,15α-dihydroxyprosta-4,5,13-trans-trienoic acid.

4-ethyl-6-methyl-9-keto-11α,15α-dihydroxyprosta-4,5,13-trans-trienoic acid and 4-propyl-6-methyl-9-keto-11α,15α-dihydroxyprosta-4,5,13-trans-trienoic acid.

PREPARATION 14

A. To a solution of 500 mg. of 8R-9-keto-11α,15α-dihydroxyprosta-4,5,13-trans-trienoic acid in 10 ml. of methylene chloride is added an excess of ethereal diazomethane and the reaction mixture is kept at room temperature for 30 minutes. It is then evaporated to dryness under vacuo, to yield 8R-9-keto-11α,15α-dihydroxyprosta-4,5,13-trans-trienoic acid methyl ester.

B. To a solution of 400 mg. of 8R-9-keto-11α,15α-dihydroxyprosta-4,5,13-trans-trienoic acid methyl ester in 3 ml. of methanol is added a solution of 400 mg. of hydroxylamine hydrochloride and 500 mg. of sodium acetate in 10 ml. of methanol-water (1:1). The resulting reaction mixture is kept at room temperature for 18 hours under an argon atmosphere and the solvent is then eliminated under reduced pressure. The residue is taken up in water and the mixture extracted with ethyl acetate, the organic phase is separated, washed with saturated sodium chloride solution, dried over magnesium sulfate and evaporated to dryness under vacuo, thus obtaining 8R-9-hydroxyimino-11α,15α-dihydroxyprosta-4,5,13-trans-trienoic acid methyl ester.

C. To a solution of 400 mg. of 8R-9-hydroxyimino-11α,15α-dihydroxyprosta-4,5,13-trans-trienoic acid methyl ester in 8 ml. of anhydrous tetrahydrofuran is added 1.6 g. of activated manganese dioxide, and the reaction mixture is stirred at room temperature for 6 hours, the manganese dioxide is filtered off and washed with acetone and the combined filtrates are evaporated to dryness under reduced pressure. The residue is redissolved in tetrahydrofuran and stirred with another 1.6 g. batch of manganese dioxide as above, repeating the operation twice. After final evaporation of the solvent and purification of the residue by chromatography on Florisil there is obtained the pure 8R-9-hydroxyimino-11α-hydroxy-15-keto-prosta-4,5,13-trans-trienoic acid methyl ester.

D. To 280 mg. of 8R-9-hydroxyimino-11α-hydroxy-15-ketoprosta-4,5,13-trans-trienoic acid methyl ester are added 6 ml. of a (1:1) mixture of N-trimethylsilyl-diethylamine and anhydrous acetone, and the reaction mixture is kept at room temperature, under an argon atmosphere for 6 hours. The reaction mixture is then evaporated to dryness under reduced pressure and the oily residue is dissolved in 10 ml. of anhydrous tetrahydrofuran. The resulting solution is cooled to −78°C and treated dropwise, under an argon atmosphere with 1.4 ml. of 2N methylmagnesium bromide in ether, maintaining the temperature of the reaction mixture below −60°C. The reaction mixture is stirred at −78°C for 5 hours further, diluted with saturated ammonium chloride solution and extracted with ether. The organic extract is washed with saturated ammonium chloride solution, dried over magnesium sulfate and evaporated to dryness under vacuo. The residue is dissolved in 10 ml. of 70% aqueous methanol and treated with 0.1 ml. of a mixture of acetic acid-water (0.2:3) and the reaction mixture is kept at 0°C for 18 hours. It is then evaporated to dryness under vacuo and the residue purified by thin layer chromatography using ethyl acetate-ether (75:25) as eluant, thus obtaining the individual isomers, i.e., 8R-9-hydroxyimino-11α,15α-dihydroxy-15β-methylprosta-4,5,13-trans-trienoic acid methyl ester and 8R-9-hydroxyimino-11α,15β-dihydroxy-15α-methylprosta-4,5,13-trans-trienoic acid methyl ester in pure form.

E. To a stirred solution of 150 mg. of 8R-9-hydroxyimino-11α,15α-dihydroxy-15β-methylprosta-4,5,13-trans-trienoic acid methyl ester in 3 ml. of methanol is added a solution of 150 mg. of thallium (III) nitrate in 3 ml. of methanol. The reaction mixture is stirred at room temperature for 10 minutes, and the formed precipitate separated by filtration and washed with methanol. To the filtrate are added 5 ml. of dilute acetic acid and the mixture is stirred for 5 minutes, it is then extracted with ether and the organic extract washed with saturated sodium chloride solution, dried over magnesium sulfate and evaporated to dryness under reduced pressure. The residue is purified by chromatography on Florisil. The fractions eluted with diethyl ether-ethyl acetate (9:1) afford the pure 8R-9-keto-11α,15α-dihydroxy-15β-methylprosta-4,5,13-trans-trienoic acid methyl ester [8R-antimer of the methyl ester of (10), R and $R^5$ = H; $R^6$ = β-Me; $n$ = 4]

Similarly, 8R-9-hydroxyimino-11α,15β-dihydroxy-15α-methylprosta-4,5,13-trans-trienoic acid methyl ester is converted into 8R-9-keto-11α,15β-dihydroxy-15α-methylprosta-4,5,13-trans-trienoic acid methyl ester.

By repeating the procedures described in this Preparation but using as starting materials in Part A the compounds listed below:

8R-4-methyl-9-keto-11α,15α-dihydroxyprosta-4,5,13-trans-trienoic acid,
8R-6-methyl-9-keto-11α,15α-dihydroxyprosta-4,5,13-trans-trienoic acid,
8R-4,6-dimethyl-9-keto-11α,15α-dihydroxyprosta-4,5,13-trans-trienoic acid,
8R-4-propyl-6-methyl-9-keto-11α,15α-dihydroxyprosta-4,5,13-trans-trienoic acid,
8R-9-keto-11α,15α-dihydroxy-20-ethylprosta-4,5,13-trans-trienoic acid,
8R-6-ethyl-9-keto-11α,15α-dihydroxy-20-norprosta-4,5,13-trans-trienoic acid,
8R-6-methyl-9-keto-11α,15α-dihydroxy-20-pentylprosta-4,5,13-trans-trienoic acid,
9-keto-11α,15α-dihydroxyprosta-4,5,13-trans-trienoic acid,
9-keto-11α,15α-dihydroxy-20-ethylprosta-4,5,13-trans-trienoic acid,
4-methyl-9-keto-11α,15α-dihydroxyprosta-4,5,13-trans-trienoic acid,
6-methyl-9-keto-11α,15α-dihydroxyprosta-4,5,13-trans-trienoic acid,
4,6-dimethyl-9-keto-11α,15α-dihydroxyprosta-4,5,13-trans-trienoic acid,
4-methyl-9-keto-11α,15α-dihydroxy-20-ethylprosta-4,5,13-trans-trienoic acid,
6-methyl-9-keto-11α,15α-dihydroxy-20-ethylprosta-4,5,13-trans-trienoic acid,
6-methyl-9-keto-11α,15α-dihydroxy-20-norprosta-4,5,13-trans-trienoic acid and
4-propyl-6-methyl-9-keto-11α,15α-dihydroxyprosta-4,5,13-trans-trienoic acid, there are obtained as final products:

8R-4,15β-dimethyl-9-keto-11α,15α-dihydroxyprosta-4,5,13-trans-trienoic acid methyl ester and 8R-4,15α-dimethyl-9-keto-11α,15β-dihydroxyprosta-4,5,13-trans-trienoic acid methyl ester;
8R-6,15β-dimethyl-9-keto-11α,15α-dihydroxyprosta-4,5,13-trans-trienoic acid methyl ester and 8R-6,15α-dimethyl-9-keto-11α,15β-dihydroxyprosta-4,5,13-trans-trienoic acid methyl ester;
8R-4,6,15β-trimethyl-9-keto-11α,15α-dihydroxyprosta-4,5,13-trans-trienoic acid methyl ester and 8R-4,6,15α-trimethyl-9-keto-11α,15β-dihydroxyprosta-4,5,13-trans-trienoic acid methyl ester;
8R-4-propyl-6,15β-dimethyl-9-keto-11α,15α-dihydroxyprosta-4,5,13-trans-trienoic acid methyl ester and 8R-4-propyl-6,15α-dimethyl-9-keto-11α,15β-dihydroxyprosta-4,5,13-trans-trienoic acid methyl ester;
8R-9-keto-11α,15α-dihydroxy-15β-methyl-20-ethylprosta-4,5,13-trans-trienoic acid methyl ester and 8R-9-keto-11α,15β-dihydroxy-15α-methyl-20-ethylprosta-4,5,13-trans-trienoic acid methyl ester;
8R-6-ethyl-15β-methyl-9-keto-11α,15α-dihydroxy-20-norprosta-4,5,13-trans-trienoic acid methyl ester and 8R-6-ethyl-15α-methyl-9-keto-11α,15β-dihydroxy-20-norprosta-4,5,13-trans-trienoic acid methyl ester;
8R-6,15β-dimethyl-9-keto-11α,15α-dihydroxy-20-pentylprosta-4,5,13-trans-trienoic acid methyl ester and 8R-6,15α-dimethyl-9-keto-11α,15β-dihydroxy-20-pentylprosta-4,5,13-trans-trienoic acid methyl ester;
9-keto-11α,15α-dihydroxy-15β-methylprosta-4,5,13-trans-trienoic acid methyl ester and 9-keto-11α,15β-dihydroxy-15α-methylprosta-4,5,13-trans-trienoic acid methyl ester;
9-keto-11α,15α-dihydroxy-15β-methyl-20-ethylprosta-4,5,13-trans-trienoic acid methyl ester and 9-keto-11α,15β-dihydroxy-15α-methyl-20-ethylprosta-4,5,13-trans-trienoic acid methyl ester;
4,15β-dimethyl-9-keto-11α,15α-dihydroxyprosta-4,5,13-trans-trienoic acid methyl ester and 4,15α-dimethyl-9-keto-11α,15β-dihydroxyprosta-4,5,13-trans-trienoic acid methyl ester;
6,15β-dimethyl-9-keto-11α,15α-dihydroxyprosta-4,5,13-trans-trienoic acid methyl ester and 6,15α-dimethyl-9-keto-11α,15β-dihydroxyprosta-4,5,13-trans-trienoic acid methyl ester;
4,6,15β-trimethyl-9-keto-11α,15α-dihydroxyprosta-4,5,13-trans-trienoic acid methyl ester and 4,6,15α-trimethyl-9-keto-11α,15β-dihydroxyprosta-4,5,13-trans-trienoic acid methyl ester;
4,15β-dimethyl-9-keto-11α,15α-dihydroxy-20-ethylprosta-4,5,13-trans-trienoic acid methyl ester and 4,15α-dimethyl-9-keto-11α,15β-dihydroxy-20-ethylprosta-4,5,13-trans-trienoic acid methyl ester;
6,15β-dimethyl-9-keto-11α,15α-dihydroxy-20-ethylprosta-4,5,13-trans-trienoic acid methyl ester and 6,15α-dimethyl-9-keto-11α,15β-dihydroxy-20-ethylprosta-4,5,13-trans-trienoic acid methyl ester;
6,15β-dimethyl-9-keto-11α,15α-dihydroxy-20-norprosta-4,5,13-trans-trienoic acid methyl ester, and 6,15α-dimethyl-9-keto-11α,15β-dihydroxy-20-norprosta-4,5,13-trans-trienoic acid and
4-propyl-6,15β-dimethyl-9-keto-11α,15α-dihydroxyprosta-4,5,13-trans-trienoic acid methyl ester and 4-propyl-6,15α-dimethyl-9-keto-11α,15β-dihydroxyprosta-4,5,13-trans-trienoic acid methyl ester, respectively.

Likewise, but using ethylmagnesium bromide and propylmagnesium bromide in lieu of methylmagnesium bromide in part D of this Preparation, the corresponding 15-ethyl and 15-propyl compounds are obtained.

PREPARATION 15

A. A suspension of 4 g. of crude pancreatic lipase (Sigma L-3126) in 40 ml. of a 0.1M sodium chloride and 0.05M calcium chloride solution in water is stirred at 25°C for 1 hour. The mixture is then centrifuged for 1 hour at 5000 rev/min and at 25° to 30°C. The supernatant is neutralized with 1N sodium hydroxide solution to pH 7.2 to 7.4 and used directly for the hydrolysis of the prostaglandin derivatives of the invention.

B. Forty-two milligrams of 8R-9-keto-11α,15α-dihydroxy-15β-methylprosta-4,5,13-trans-trienoic acid methyl ester are dissolved by sonication at 37°C for 20 minutes in 30 ml. of the lipase solution prepared as described in part A. The reaction mixture is magnetically stirred for 15 minutes at 25° to 27°C, adjusting constantly the pH at 7.2 to 7.4 during the reaction period with 1N sodium hydroxide solution. The reaction mixture is cooled to 0°C and acidified to pH 5, and the product extracted several times from the solution with ethyl acetate and ether. The combined organic extracts are dried over magnesium sulfate and evaporated to dryness under vacuo. The residue is dissolved in methylene chloride and chromatographed on 3 g. of Florisil. The column is eluted successively with methylene chloride-diethyl ether mixtures, diethyl ether, diethyl ether-ethyl acetate mixtures, pure ethyl acetate and ethyl acetate-methanol (80:20). The fractions eluted with the latter solvent mixture afford the pure 8R-9-keto-11α,15α -dihydroxy-15β-methylprosta-4,5,13-trans-trienoic acid [8R-antimer of (10), R and $R^5$ = H; $R^6$ = β-Me; $n$ = 4].

In a similar manner by following the above procedure, the remaining methyl ester compounds obtained in Preparation 14 are converted into the corresponding free prostatrienoic acids.

PREPARATION 16

Preparations 3 through 9 are repeated using 1'R-[2'α-hydroxy-4'α-p-phenylbenzoyloxy-5'β-(3"β-hydroxyoct-1"(t)-en-1"-yl) cyclopent-1'α-yl]-acetic acid 1,2'-lactone as starting material obtaining successively:

1'R-[2'α,4'α-dihydroxy-5'β-(3"β-hydroxyoct-1"(t)-en-1"-yl) cyclopent-1'α-yl]-acetic acid 1,2'-lactone, 1'R-[2'α-hydroxy-4'α-tetrahydropyranyloxy-5'β-(3"β-tetrahydropyranyloxyoct-1"(t)-en-1"-yl) cyclopent-1'α-yl]-acetic acid 1,2'-lactone, 1'R-[2'α-hydroxy-4'α-tetrahydropyranyloxy-5'β-(3"β-tetrahydropyranyloxyoct-1"(t)-en-1"-yl) cyclopent-1'α-yl]-acetaldehyde 1,2'-hemiacetal, 8R-1,6{,9α-trihydroxy-11α,15β-bistetrahydropyranyloxyprost-4-yn-13-trans-ene, 8R-1,6{,9α-triacetoxy-11α,15β-bistetrahydropyranyloxyprost-4-yn-13-trans-ene, 8R-1,9α-diacetoxy-11α,15β-bistetrahydropyranyloxyprosta-4,5,13-trans-triene, 8R-1,9α-dihydroxy-11α,15β-bistetrahydropyranyloxyprosta-4,5,13-trans-triene and 8R-9-keto-11α,15β-dihydroxyprosta-4,5,13-trans-trienoic acid.

The latter compound is then submitted to the reactions described in Preparation 14 parts A, B and C, to produce 8R-9-hydroxyimino-11α-hydroxy-15-ketoprosta-4,5,13-trans-trienoic acid methyl ester, identical to the compound obtained in part C of said Preparation.

EXAMPLE 1

A solution of 250 mg. of 8R-9-keto-11α,15α-dihydroxyprosta-4,5,13-trans-trienoic acid in 10 ml. of methanol is cooled to 0°C and treated dropwise under argon atmosphere, with 10 ml. of a 1N solution of sodium hydroxide in methanol-water (1:1). The reaction mixture is allowed to warm to room temperature and stirred at this temperature, following the course of the reaction by t.l.c. and ultraviolet absorption determination in aliquots taken every ten minutes. After 1 hour the reaction mixture is diluted with water, acidified with hydrochloric acid to pH 2, and extracted three times with methylene chloride. The combined organic extracts are dried over magnesium sulfate and evaporated to dryness under vacuo. The oily residue is purified by chromatography on silica gel, to obtain 8R-9-keto-15α-hydroxyprosta-4,5,10,13-trans-tetraenoic acid (8R-antimer of II, R, $R^5$ and $R^{4'}$ = H;

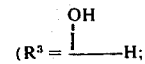

$n$ = 4) and small amount of 9-keto-15α-hydroxyprosta-4,5,8(12),13-transtetraenoic acid in pure form (III, R, $R^5$ and $R^{4'}$ = H;

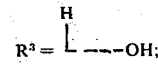

$n$ = 4).

By the same method, 8R-4-ethyl-9-keto-11α,15α-dihydroxyprosta-4,5,13-trans-trienoic acid, 8R-4-propyl-9-keto-11α,15α-dihydroxyprosta-4,5,13-trans-trienoic acid, 8R-4-methyl-9-keto-11α,15α-dihydroxy-20-bisnorprosta-4,5,13-trans-trienoic acid, and 8R-4,20-dimethyl-9-keto-11α,15α-dihydroxyprosta-4,5,13-trans-trienoic acid, are converted respectively into:

8R-4-ethyl-9-keto-15α-hydroxyprosta-4,5,10,13-trans-tetra enoic acid, 8R-4-propyl-9-keto-15α-hydroxyprosta-4,5,10,13-trans-tetraenoic acid, 8R-4-methyl-9-keto-15α-hydroxy-20-bisnorprosta-4,5,10,13-trans-tetraenoic acid and 8R-4,20-dimethyl-9-keto-15α-hydroxyprosta-4,5,10,13-trans-tetraenoic acid, obtaining in each case a small amount of the corresponding prosta-4,5,8(12),13-trans-tetraenoic acid isomeric compounds.

EXAMPLE 2

A mixture of 85 mg. of 8R-9-keto-11α,15α-dihydroxyprosta-4,5,13-trans-trienoic acid and 3 ml. of 90% aqueous acetic acid is stirred at 60°C, under an atmosphere of argon for 18 hours. The solvent is then eliminated under reduced pressure, at a temperature not higher than 20°C. The oily residue is dissolved in methylene chloride and purified by chromatography on Florisil. The fractions eluted with ethyl acetate and ethyl acetate-methanol (9:1) afford the pure 8R-9-keto-15α-hydroxyprosta-4,5,10,13-trans-tetraenoic acid, identical to the compound obtained in Example 1.

In a similar manner, starting from
8R-9-keto-11α,15α-dihydroxy-20-bisnorprosta-4,5,13-trans-trienoic acid,
8R-9-keto-11α,15α-dihydroxy-20-norprosta-4,5,13-trans-trienoic acid,
8R-9-keto-11α,15α-dihydroxy-20-methylprosta-4,5,13-trans-trienoic acid,
8R-9-keto-11α,15α-dihydroxy-20-ethylprosta-4,5,13-trans-trienoic acid,
8R-9-keto-11α,15α-dihydroxy-20-pentylprosta-4,5,13-trans-trienoic acid,
8R-4-methyl-9-keto-11α,15α-dihydroxyprosta-4,5,13-trans-trienoic acid,
8R-4-methyl-9-keto-11α,15α-dihydroxy-20-norprosta-4,5,13-trans-trienoic acid,
8R-4-methyl-9-keto-11α,15α-dihydroxy-20-ethylprosta-4,5,13-trans-trienoic acid,
8R-6-methyl-9-keto-11α,15α-dihydroxyprosta-4,5,13-trans-trienoic acid,
8R-6-methyl-9-keto-11α,15α-dihydroxy-20-bisnorprosta-4,5,13-trans-trienoic acid,
8R-6,20-dimethyl-9-keto-11α,15α-dihydroxyprosta-4,5,13-trans-trienoic acid,
8R-6-methyl-9-keto-11α,15α-dihydroxy-20-pentylprosta-4,5,13-trans-trienoic acid,
8R-4,6-dimethyl-9-keto-11α,15α-dihydroxyprosta-4,5,13-trans-trienoic acid and
8R-4-ethyl-6-methyl-9-keto-11α,15α-dihydroxyprosta-4,5,13-trans-trienoic acid, there are produced, respectively:
8R-9-keto-15α-hydroxy-20-bisnorprosta-4,5,10,13-trans-tetraenoic acid,
8R-9-keto-15α-hydroxy-20-norprosta-4,5,10,13-trans-tetraenoic acid,
8R-9-keto-15α-hydroxy-20-methylprosta-4,5,10,13-trans-tetraenoic acid,
8R-9-keto-15α-hydroxy-20-ethylprosta-4,5,10,13-trans-tetraenoic acid,
8R-9-keto-15α-hydroxy-20-pentylprosta-4,5,10,13-trans-tetraenoic acid,
8R-4-methyl-9-keto-15α-hydroxyprosta-4,5,10,13-trans-tetraenoic acid,
8R-4-methyl-9-keto-15α-hydroxy-20-norprosta-4,5,10,13-trans-tetraenoic acid,
8R-4-methyl-9-keto-15α-hydroxy-20-ethylprosta-4,5,10,13-trans-tetraenoic acid,
8R-6-methyl-9-keto-15α-hydroxyprosta-4,5,10,13-trans-tetraenoic acid,
8R-6-methyl-9-keto-15α-hydroxy-20-bisnorprosta-4,5,10,13-trans-tetraenoic acid,
8R-6,20-dimethyl-9-keto-15α-hydroxyprosta-4,5,10,13-trans-tetraenoic acid,
8R-6-methyl-9-keto-15α-hydroxy-20-pentylprosta-4,5,10,13-trans-tetraenoic acid,
8R-4,6-dimethyl-9-keto-15α-hydroxyprosta-4,5,10,13-trans-tetraenoic acid and
8R-4-ethyl-6-methyl-9-keto-15α-hydroxyprosta-4,5,10,13-trans-tetraenoic acid.

EXAMPLE 3

A solution of 125 mg. of 8R-9-keto-11α,15α-dihydroxy-15β-methylprosta-4,5,13-trans-trienoic acid in 5 ml. of methanol is cooled to 0°C and treated dropwise under argon atmosphere with 5 ml. of a 1N solution of sodium hydroxide in methanol-water (1:1). The reaction mixture is allowed to warm to room temperature under stirring, taking aliquots at 10 minutes intervals to determine the ultraviolet spectrum. After 1 hour, the reaction mixture is diluted with water, cooled to 5°C and acidified with 10% aqueous acetic acid. The reaction mixture is then extracted 3 times with methylene chloride and the combined organic extracts are washed well with saturated sodium chloride solution, dried over magnesium sulfate and evaporated to dryness under reduced pressure. Purification of the residue by chromatography on silica gel affords the pure 8R-9-keto-15α-methyl-15α-hydroxyprosta-4,5,10,13-trans-tetraenoic acid (8R-antimer of II, R, $R^5$ and $R^{4'}$ = H;

$$R^3 = \overset{Me}{\underset{\phantom{|}}{|}}---OH;$$

$n = 4$) and a small amount of 9-keto-15β-methyl-15α-hydroxyprosta-4,5,8(12),13-trans-tetraenoic acid (III, R, $R^5$ and $R^{4'}$ = H;

$$R^3 = \overset{Me}{\underset{\phantom{|}}{|}}---OH;$$

$n = 4$).

In a similar manner, but using 8R-4,15β-dimethyl-9-keto-11α,15α-dihydroxyprosta-4,5,13-trans-trienoic acid,
8R-6,15β-dimethyl-9-keto-11α,15α-dihydroxyprosta-4,5,13-trans-trienoic acid,
8R-4,6,15β-trimethyl-9-keto-11α,15α-dihydroxyprosta-4,5,13-trans-trienoic acid,
8R-4-propyl-6,15β-dimethyl-9-keto-11α,15α-dihydroxyprosta-4,5,13-trans-trienoic acid,
8R-15β-methyl-9-keto-11α,15α-dihydroxy-20-ethylprosta-4,5,13-trans-trienoic acid,
8R-6-ethyl-15β-methyl-9-keto-11α,15α-dihydroxy-20-norprosta-4,5,13-trans-trienoic acid,
8R-6,15β-dimethyl-9-keto-11α,15α-dihydroxy-20-pentylprosta-4,5,13-trans-trienoic acid,
8R-15β-ethyl-9-keto-11α,15α-dihydroxyprosta-4,5,13-trans-trienoic acid and
8R-15β-propyl-9-keto-11α,15α-dihydroxyprosta-4,5,13-trans-trienoic acid as starting materials there are respectively obtained:
8R-4,15β-dimethyl-9-keto-15α-hydroxyprosta-4,5,10,13-trans-tetraenoic acid,
8R-6,15β-dimethyl-9-keto-15α-hydroxyprosta-4,5,10,13-trans-tetraenoic acid,
8R-4,6,15β-trimethyl-9-keto-15α-hydroxyprosta-4,5,10,13-trans-tetraenoic acid,
8R-4-propyl-6,15β-dimethyl-9-keto-15α-hydroxyprosta-4,5,10,13-trans-tetraenoic acid,
8R-15β-methyl-9-keto-15α-hydroxy-20-ethylprosta-4,5,10,13-trans-tetraenoic acid,
8R-6-ethyl-15β-methyl-9-keto-15α-hydroxy-20-norprosta-4,5,10,13-trans-tetraenoic acid,
8R-6,15β-dimethyl-9-keto-15α-hydroxy-20-pentylprosta-4,5,10,13-trans-tetraenoic acid,
8R-15β-ethyl-9-keto-15α-hydroxyprosta-4,5,10,13-trans-tetraenoic acid and
8R-15β-propyl-9-keto-15α-hydroxyprosta-4,5,10,13-trans-tetraenoic acid, and small amounts of the corresponding prosta-4,5,8(12),13-trans-tetraenoic acid isomeric compounds.

Likewise, starting from the corresponding 8R-15α-alkyl-15β-hydroxyprosta-4,5,13-trans-trienoic acids there are obtained the respective 8R-15α-alkyl-15β- hydroxyprosta-4,5,10,13-trans-tetraenoic acid derivatives as main products.

EXAMPLE 4

A solution of 250 mg. of 8R-9-keto-15α-hydroxyprosta-4,5,10,13-tetraenoic acid in 10 ml. of methanol is cooled to 0°C and treated dropwise under argon atmosphere, with 10 ml. of a 1N solution of sodium hydroxide in methanol-water (1:1). The reaction mixture is allowed to warm to room temperature and stirred for 8 hours under these conditions. It is then diluted with water, acidified with hydrochloric acid to pH-2 and extracted several times with methylene chloride. The combined organic extracts are dried over magnesium sulfate and evaporated to dryness under vacuo. The oily residue is purified by chromatography on silica gel, to produce the pure 9-keto-15α-hydroxyprosta-4,5,8(12),13-trans-tetraenoic acid (III, R, $R^5$ and $R^{4'}$ = H;

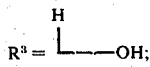

$n = 4$).

In a similar manner starting from 8R-9-keto-15β-methyl-15α-hydroxyprosta-4,5,10,13-trans-tetraenoic acid but using dilute acetic acid instead of hydrochloric acid for liberating the free prostaglandin derivative from its sodium salt formed during the reaction with sodium hydroxide, there is obtained 9-keto-15β-methyl-15α-hydroxyprosta-4,5,8(12),13-trans-tetraenoic acid (III, R, $R^5$ and $R^{4'}$ = H;

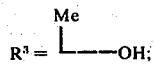

$n = 4$).

EXAMPLE 5

To previously cooled solution (0°C) of 125 mg. of 9-keto-11α,15α-dihydroxyprosta-4,5,13-trans-trienoic acid in 5 ml. of methanol is added dropwise, under stirring and under argon atmosphere, 5 ml. of a 1N solution of sodium hydroxide in methanol, and the resulting solution is stirred at room temperature for 12 hours. The reaction mixture is then worked up as described in Example 4, thus obtaining 9-keto-15α-hydroxyprosta-4,5,8(12),13-trans-tetraenoic acid, identical to the product obtained in Example 4.

In another experiment the reaction mixture is maintained for 3 hours at 37°C, obtaining the same results.

EXAMPLE 6

By following the methods of Examples 4 or 5 starting from the corresponding 9-keto-11α,15α-dihydroxyprosta-4,5,13-trans-trienoic acid derivatives having additional alkyl groups at C-4, C-6 and/or C-15 or the corresponding 11-desoxy-10-dehydro analogs thereof there are produced the following compounds:

4-methyl-9-keto-15α-hydroxyprosta-4,5,8(12),13-trans-tetraenoic acid,
6-methyl-9-keto-15α-hydroxyprosta-4,5,8(12),13-trans-tetraenoic acid,
4,6-dimethyl-9-keto-15α-hydroxyprosta-4,5,8(12),13-trans-tetraenoic acid,
9-keto-15α-hydroxy-20-bisnorprosta-4,5,8(12),13-trans-tetraenoic acid,
9-keto-15α-hydroxy-20-ethylprosta-4,5,8(12),13-trans-tetraenoic acid,
9-keto-15α-hydroxy-20-pentylprosta-4,5,8(12),13-trans-tetraenoic acid,
6-methyl-9-keto-15α-hydroxy-20-bisnorprosta-4,5,8(12),13-trans-tetraenoic acid,
4-methyl-9-keto-15α-hydroxy-20-norprosta-4,5,8(12),13-trans-tetraenoic acid,
4-methyl-9-keto-15α-hydroxy-20-ethylprosta-4,5,8(12),13-trans-tetraenoic acid,
4,15β-dimethyl-9-keto-15α-hydroxyprosta-4,5,8(12),13-trans-tetraenoic acid,
6,15β-dimethyl-9-keto-15α-hydroxyprosta-4,5,8(12),13-trans-tetraenoic acid,
4,6,15β-trimethyl-9-keto-15α-hydroxyprosta-4,5,8(12),13-trans-tetraenoic acid,
4-propyl-6,15β-dimethyl-9-keto-15α-hydroxyprosta-4,5,8(12),13-trans-tetraenoic acid,
15β-methyl-9-keto-15α-hydroxy-20-ethylprosta-4,5,8(12),13-trans-tetraenoic acid,
6-ethyl-15β-methyl-9-keto-15α-hydroxy-20-norprosta-4,5,8(12),13-trans-tetraenoic acid,
6,15β-dimethyl-9-keto-15α-hydroxy-20-pentylprosta-4,5,8(12),13-trans-tetraenoic acid,
15β-ethyl-9-keto-15α-hydroxyprosta-4,5,8(12),13-trans-tetraenoic acid, and
15β-propyl-9-keto-15α-hydroxyprosta-4,5,8(12),13-trans-tetraenoic acid, as well as the 15α-alkyl-15β-hydroxy isomers of compounds having said substitution.

EXAMPLE 7

To a solution of 200 mg. of 8R-9-keto-15α-hydroxyprosta-4,5,10,13-trans-tetraenoic acid in 5 ml. of methylene chloride is added an excess of ethereal diazomethane, and the reaction mixture is kept at room temperature for 30 minutes. It is then evaporated to dryness under vacuo, to yield 8R-9-keto-15α-hydroxyprosta-4,5,10,13-trans-tetraenoic acid methyl ester. (II, R and $R^5$ = H;

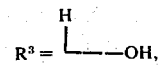

$R^4$ = Me; $n = 4$)

By the same method but using diazoethane or diazopropane in place of diazomethane there are produced 8R-9-keto-15α-hydroxyprosta-4,5,10,13-trans-tetraenoic acid ethyl ester and 8R-9-keto-15α-hydroxyprosta-4,5,10,13-trans-tetraenoic acid propyl ester, respectively.

In a similar manner, the other prostatetraenoic acid derivatives obtained in the previous Examples are converted into the corresponding methyl, ethyl, or propyl esters. Representative compounds thus obtained are:
8R-4-methyl-9-keto-15α-hydroxyprosta-4,5,10,13-trans-tetraenoic acid methyl ester,
8R-6-methyl-9-keto-15α-hydroxyprosta-4,5,10,13-trans-tetraenoic acid methyl ester,
8R-4,6-dimethyl-9-keto-15α-hydroxyprosta-4,5,10,13-trans-tetraenoic acid methyl ester,
8R-15β-methyl-9-keto-15α-hydroxyprosta-4,5,10,13-trans-tetraenoic acid ethyl ester,
8R-4,15β-dimethyl-9-keto-15α-hydroxyprosta-4,5,10,13-trans-tetraenoic acid propyl ester, 8R-9-keto-15α-hydroxy-20-ethylprosta-4,5,10,13-trans-tetraenoic acid methyl ester, 8R-4-methyl-9-keto-11α,15α-dihydroxy-20-norprosta-4,5,10,13-trans-tetraenoic acid ethyl ester, 9-keto-15α-hydroxyprosta-4,5,8(12),13-trans-tetraenoic acid methyl ester, 4-methyl-9-keto-15α-hydroxyprosta-4,5,8(12),13-trans-tetraenoic acid methyl ester, 6-methyl-S-keto-15α-hydroxyprosta-4,5,8(12),13-trans-tetraenoic acid methyl ester, 4,6-dimethyl-9-keto-15α-hydroxyprosta-4,5,8(12),13-trans-tetraenoic acid methyl ester, 15β-methyl-9-keto-15α-hydroxyprosta-4,5,8(12),13-trans-tetraenoic acid ethyl ester, 6,15β-dimethyl-9-keto-15α-hydroxyprosta-4,5,8(12),13-trans-tetraenoic acid ethyl ester, 9-keto-15α-hydroxy-20-bisnorprosta-4,5,8(12),13-trans-tetraenoic acid propyl ester, 9-keto-15α-hydroxy-20-ethylprosta-4,5,8(12),13-trans-tetraenoic acid methyl ester and 6-ethyl-15β-methyl-9-keto-15α-hydroxy-20-norprosta-4,5, 8(12),13-trans-tetraenoic acid ethyl ester.

EXAMPLE 8

To a solution of 200 mg. of 8R-9-koto-15α-hydroxyprosta-4,5,10,13-trans-tetraenoic acid methyl ester in 10 ml. of methanol, cooled to 0°C is added 100 mg. of sodium borohydride, and the reaction mixture is stirred at room temperature for 30 minutes. The solvent is then eliminated under reduced pressure, water is added and the product extracted with ethyl acetate. The organic extract is washed with 50% saturated sodium chloride solution and water to neutral, dried over magnesium sulfate and evaporated to dryness under reduced pressure. The residue is purified by chromatography on silica gel using methylene chloride-ethyl acetate mixtures to thus obtain 8R-9α,15α-dihydroxyprosta-4,5,10,13-trans-tetraenoic acid methyl ester and 8R-9β,15α-dihydroxyprosta-4,5,10,13-trans-tetraenoic acid methyl ester in approximately equal amounts (8R-antimers of IV, R and R⁵ = H;

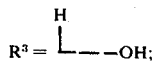

R⁴′= Me; n = 4).

In a similar manner from the corresponding 9-ketoprostatetraenoic acid alkyl ester compounds there are obtained:

8R-9α,15α-dihydroxy-20-bisnorprosta-4,5,10,13-trans-tetraenoic acid methyl ester and 8R-9β,15α-dihydroxy-20-bisnorprosta-4,5,10,13-trans-tetraenoic acid methyl ester;

8R-9α,15α-dihydroxy-20-ethylprosta-4,5,10,13-trans-tetraenoic acid methyl ester and 8R-9β,15α-dihydroxy-20-ethylprosta-4,5,10,13-trans-tetraenoic acid methyl ester;

8R-9α,15α-dihydroxy-20-pentylprosta-4,5,10,13-trans-tetraenoic acid methyl ester and 8R-9β,15α-dihydroxy-20-pentylprosta-4,5,10,13-trans-tetraenoic acid methyl ester;

8R-4-methyl-9α,15α-dihydroxyprosta-4,5,10,13-trans-tetraenoic acid methyl ester and 8R-4-methyl-9β,15α-dihydroxyprosta-4,5,10,13-trans-tetraenoic acid methyl ester;

8R-6-methyl-9α,15α-dihydroxyprosta-4,5,10,13-trans-tetraenoic acid methyl ester and 8R-6-methyl-9β,15α-dihydroxyprosta-4,5,10,13-trans-tetraenoic acid methyl ester;

8R-4,6-dimethyl-9α,15α-dihydroxyprosta-4,5,10,13-trans-tetraenoic acid methyl ester and 8R-4,6-dimethyl-9β,15α-dihydroxyprosta-4,5,10,13-trans-tetraenoic acid methyl ester;

8R-6-methyl-9α,15α-dihydroxy-20-ethylprosta-4,5,10,13-trans-tetraenoic acid methyl ester and 8R-6-methyl-9β,15α-dihydroxy-20-ethylprosta-4,5,10,13-trans-tetraenoic acid methyl ester;

8R-6,20-dimethyl-9α,15α-dihydroxyprosta-4,5,10,13-trans-tetraenoic acid methyl ester and 8R-6,20-dimethyl-9β,15α-dihydroxyprosta-4,5,10,13-trans-tetraenoic acid methyl ester;

8R-15β-methyl-9α,15α-dihydroxyprosta-4,5,10,13-trans-tetraenoic acid ethyl ester and 8R-15β-methyl-9β,15α-dihydroxyprosta-4,5,10,13-trans-tetraenoic acid ethyl ester;

8R-4,15β-dimethyl-9α,15α-dihydroxyprosta-4,5,10,13-trans-tetraenoic acid ethyl ester and 8R-4,15β-dimethyl-9β,15α-dihydroxyprosta-4,5,10,13-trans-tetraenoic acid ethyl ester;

8R-6,15β-dimethyl-9α,15α-dihydroxyprosta-4,5,10,13-trans-tetraenoic acid ethyl ester and 8R-6,15β-dimethyl-9β,15α-dihydroxyprosta-4,5,10,13-trans-tetraenoic acid ethyl ester;

8R-4,6,15β-trimethyl-9α,15α-dihydroxyprosta-4,5,10,13-trans-tetraenoic acid ethyl ester and 8R-4,6,15β-trimethyl-9β,15α-dihydroxyprosta-4,5,10,13-trans-tetraenoic acid ethyl ester;

8R-4-propyl-6,15β-dimethyl-9α, 15α-dihydroxyprosta-4,5,10,13-trans-tetraenoic acid ethyl ester and 8R-4-propyl-6,15β-dimethyl-9β,15α-dihydroxyprosta-4,5,10,13-trans-tetraenoic acid ethyl ester;

8R-15β-methyl-9α,15α-dihydroxy-20-ethylprosta-4,5,10,13-trans-tetraenoic acid propyl ester and 8R-15β-methyl-9β,15α-dihydroxy-20-ethylprosta-4,5,10,13-trans-tetraenoic acid propyl ester;

9α,15α-dihydroxyprosta-4,5,8(12),13-trans-tetraenoic acid methyl ester and 9β,15α-dihydroxyprosta-4,5,8(12),13-trans-tetraenoic acid methyl ester;

4-methyl-9α,15α-dihydroxyprosta-4,5,8(12),13-trans-tetraenoic acid ethyl ester and 4-methyl-9β,15α-dihydroxyprosta-4,5,8(12),13-trans-tetraenoic acid ethyl ester;

6-methyl-9α,15α-dihydroxyprosta-4,5,8(12),13-trans-tetraenoic acid ethyl ester and 6-methyl-9β,15α-dihydroxyprosta-4,5,8(12,13-trans-tetraenoic acid ethyl ester;

4,6-dimethyl-9α,15α-dihydroxyprosta-4,5,8(12),13-transtetraenoic acid methyl ester and 4,6-dimethyl-9β,15α-dihydroxyprosta-4,5,8(12),13-trans-tetraenoic acid methyl ester;

9α,15α-dihydroxy-20-bisnorprosta-4,5,8(12),13-trans-tetraenoic acid ethyl ester and 9β,15α-dihydroxy-20-bisnorprosta-4,5,8(12),13-trans-tetraenoic acid ethyl ester;

4-methyl-9α,15α-dihydroxy-20-ethylprosta-4,5,8(12),13-trans-tetraenoic acid propyl ester and 4-methyl-9β,15α-dihydroxy-2-ethylprosta-4,5,8(12),13-trans-tetraenoic acid propyl ester;

15β-methyl-9α,15α-dihydroxyprosta-4,5,8(12),13-trans-tetraenoic acid methyl ester and 15β-methyl-9β,15α-dihydroxyprosta-4,5,8(12),13-trans-tetraenoic acid methyl ester;

15β-ethyl-9α,15α-dihydroxyprosta-4,5,8(12),13-trans-tetraenoic acid methyl ester and 15β-ethyl- 9β,15α-dihydroxyprosta-4,5,8(12),13-trans-tetraenoic acid methyl ester;

15β-propyl-9α,15α-dihydroxyprosta-4,5,8(12),13-trans-tetraenoic acid methyl ester and 15β-propyl-9β,15α-dihydroxyprosta-4,5,8(12),13-trans-tetraenoic acid methyl ester;

4,15β-dimethyl-9α,15α-dihydroxyprosta-4,5,8(12),13-trans-tetraenoic acid methyl ester and 4,15β-dimethyl-9β,15α-dihydroxyprosta-4,5,8(12),13-trans-tetraenoic acid methyl ester;

6,15β-dimethyl-9α,15α-dihydroxyprosta-4,5,8(12),13-trans-tetraenoic acid methyl ester and 6,15β-dimethyl-9β,15α-dihydroxyprosta-4,5,8(12),13-trans-tetraenoic acid methyl ester; and 4,6,15β-trimethyl-9α,15α-dihydroxyprosta-4,5,8(12),13-trans-tetraenoic acid methyl ester and 4,6,15β-trimethyl-9β,15α-dihydroxyprosta-4,5,8(12),13-trans-tetraenoic acid methyl ester, as well as the 15α-alkyl-15β-hydroxy isomers of the compounds having said substitution.

EXAMPLE 9

A solution of 180 mg. of 9-keto-15α-hydroxyprosta-4,5,8(12),13-trans-tetraenoic acid methyl ester in 5 ml. of anhydrous ether is cooled to −20°C in a dry ice-carbon tetrachloride bath and treated, under argon atmosphere, with 12 molar equivalents of ethereal methylmagnesium bromide. The reaction mixture is stirred at 0°–5°C for 8 hours, 2 ml. of methanol are then added, and thereafter the reaction mixture is diluted with 50 ml. of ether, and the resultant solution is washed with 50% saturated sodium chloride solution, dried over magnesium sulfate and evaporated to dryness under reduced pressure. The oily residue is purified by thin layer chromatography using methylene chloride containing 0.5% of methanol as eluant, thus obtaining the pure 9β-methyl-9α,15α-dihydroxyprosta-4,5,8(12),13-trans-tetraenoic acid methyl ester and a small amount of 9α-methyl-9β,15α-dihydroxyprosta-4,5,8(12),13-trans-tetraenoic acid methyl ester [VII, R and $R^5$ = H; $R^2$ and $R^{4'}$ = Me;

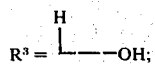

$n = 4$].

In a similar manner but using ethylmagnesium bromide and propylmagnesium bromide in lieu of methylmagnesium bromide, there are respectively obtained:

9β-ethyl-9α,15α-dihydroxyprosta-4,5,8(12),13-trans-tetraenoic acid methyl ester, 9β-propyl-9α,15α-dihydroxyprosta-4,5,8(12),13-trans-tetraenoic acid methyl ester, and small amounts of the corresponding 9α-ethyl(propyl)-9β-hydroxy isomers.

EXAMPLE 10

A solution of 180 mg. of 9-keto-15α-hydroxyprosta-4,5,8(12),13-trans-tetraenoic acid methyl ester in 5 ml. of anhydrous ether is cooled to −70°C in a dry ice-acetone bath and treated with 2.3 molar equivalents of methyllithium in ether. The reaction mixture is stirred at −70°C for 5 minutes, and the temperature is then allowed to rise to −20 °C, stirring at this temperature for 10 additional minutes; 2 ml. of methanol and 30 ml. of ether are then added and the resulting solution is washed with 50% sodium chloride solution, dried over magnesium sulfate and evaporated to dryness under vacuo. The residue is purified by thin-layer chromatography, using methylene chloride containing 0.5% of methanol as eluant, to obtain the pure 9β-methyl-9α,15α-dihydroxyprosta-4,5,8(12),13-trans-tetraenoic acid methyl ester and a small amount of the 9α-methyl-9β-hydroxy isomer, identical to the compounds obtained in Example 9.

In a similar manner, starting from 8R-9-keto-15α-hydroxyprosta-4,5,10,13-trans-tetraenoic acid methyl ester there are obtained 8R-9β-methyl-9α,15α-dihydroxyprosta-4,5,10,13-trans-tetraenoic acid methyl ester and a small quantity of the 8R-9α-methyl-9β-hydroxy isomer (8R-antimers of V, R and $R^5$ = H; $R^2$ and $R^{4'}$ = Me;

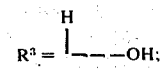

$n = 4$).

EXAMPLE 11

By following the methods of Examples 9 or 10 starting from the corresponding 9-keto compounds and using the appropriate alkylmagnesium halide or alkyllithium, there are obtained the following compounds as main products:

8R-9β-ethyl-9α,15α-dihydroxyprosta-4,5,10,13-trans-tetraenoic acid methyl ester, 8R-9β-propyl-9α,15α-dihydroxyprosta-4,5,10,13-trans-tetraenoic acid ethyl ester, 8R-9β-methyl-9α,15α-dihydroxy-20-bisnorprosta-4,5,10,13-trans-tetraenoic acid methyl ester, 8R-9β-methyl-9α,15α-dihydroxy-20-ethylprosta-4,5,10,13-trans-tetraenoic acid methyl ester, 8R-9β,20-diethyl-9α,15α-dihydroxyprosta-4,5,10,13-trans-tetraenoic acid methyl ester, 8R-9β-ethyl-9α,15α-dihydroxy-20-pentylprosta-4,5,10,13-trans-tetraenoic acid methyl ester, 8R-4,9β-dimethyl-9α,15α-dihydroxyprosta-4,5,10,13-trans-tetraenoic acid methyl ester, 8R-6,9β-dimethyl-9α,15α-dihydroxyprosta-4,5,10,13-trans-tetraenoic acid methyl ester, 8R-4,6,9β-trimethyl-9α,15α-dihydroxyprosta-4,5,10,13-trans-tetraenoic acid methyl ester, 8R-6,20-dimethyl-9β-propyl-9α,15α-dihydroxyprosta-4,5,10,13-trans-tetraenoic acid methyl ester, 8R-9β,15β-dimethyl-9α,15α-dihydroxyprosta-4,5,10,13-trans-tetraenoic acid ethyl ester, 8R-9β-ethyl-15β-methyl-9α,15α-dihydroxyprosta-4,5,10,13-trans-tetraenoic acid ethyl ester, 8R-9β-propyl-15β-methyl-9α,15α-dihydroxyprosta-4,5,10,13-trans-tetraenoic acid ethyl ester, 8R-4,6,9β,15β-tetramethyl-9α,15α-dihydroxyprosta-4,5,10,13-trans-tetraenoic acid ethyl ester, 8R-4-propyl-6,9β,15β-trimethyl-9α,15α-dihydroxyprosta-4,5,10,13-trans-tetraenoic acid ethyl ester, 8R--dimethyl-,15β-dimethgyl-9α,15α-dihydroxy-20-ethylprosta-4,5,10,13-trans-tetraenoic acid propyl ester, 4,9β-diethyl-9α,15α-dihydroxyprosta-4,5,8(12),13-trans-tetraenoic acid ethyl ester, 4,9β-dimethyl-9α,15α-dihydroxyprosta-4,5,8(12),13-trans-tetraenoic acid methyl ester, 6,9β-dimethyl-9α,15α-dihydroxyprosta-4,5,8(12),13-trans-tetraenoic acid methyl ester, 4,6,9β-trimethyl-9α,15α-dihydroxyprosta-4,5,8(12),13-trans-tetraenoic acid methyl ester,
4,6,9β,15β-tetramethyl-9α,15α-dihydroxyprosta-4,5,8(12),13-trans-tetraenoic acid methyl ester,
9β-ethyl-9α,15α-dihydroxy-20-bisnorprosta-4,5,8(12),13-trans-tetraenoic acid ethyl ester,
4,9β-dimethyl-9α,15α-dihydroxy-20-ethylprosta-4,5,8(12),13-trans-tetraenoic acid propyl ester,
9β-methyl-15β-ethyl-9α,15α-dihydroxyprosta-4,5,8(12),13-trans-tetraenoic acid methyl ester,
9β-methyl-15β-propyl-9α,15α-dihydroxyprosta-4,5,8(12),13-trans-tetraenoic acid methyl ester,
8R-9β,15α-dimethyl-9α,15β-dihydroxyprosta-4,5,10,13-trans-tetraenoic acid methyl ester,
8R-4,6,9β,15α-tetramethyl-9α,15α-dihydroxyprosta-4,5,10,13-trans-tetraenoic acid methyl ester, and
4,6,9β,15α-tetramethyl-9α,15β-dihydroxyprosta-4,5,8(12),13-trans-tetraenoic acid methyl ester, obtaining in each case small quantities of the corresponding 9α-alkyl-9β-hydroxy isomers.

EXAMPLE 12

Forty-two milligrams of 8R-9α,15α-dihydroxyprosta-4,5,10,13-trans-tetraenoic acid methyl ester are dissolved by sonication at 37°C for 20 minutes in 30 ml. of the lipase solution prepared as described in part A of preparation 15. The reaction mixture is magnetically stirred for 15 minutes at 25°C to 27°C, adjusting constantly the pH at 7.2 to 7.4 during the reaction period with 1N sodium hydroxide solution. The reaction mixture is then cooled to 0°C and acidified to pH 5 using a 0.2N hydrochloric acid solution and the product extracted several times from the solution with ethyl acetate and ether. The combined organic extracts are dried over magnesium sulfate and evaporated to dryness under vacuo. The residue is dissolved in methylene-chloride and chromatographed on 3 g. of Florisil. The column is eluted successively with methylene chloride-diethyl ether mixtures, diethyl ether, diethyl ether-ethyl acetate mixtures, pure ethyl acetate and ethyl acetate-methanol (80:20). The fractions eluted with the latter solvent mixture afford the pure 8R-9α,15α-dihydroxyprosta-4,5,10,13-trans-tetraenoic acid. (8R-antimer of IV, R, R⁵ and R⁴' = H;

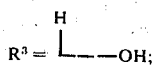

$n = 4$)

In a similar manner by following the above procedure, from the corresponding alkyl esters obtained in Examples 8, 10 and 11 there are produced the following free prostaglandin derivatives:
8R-9β,15α-dihydroxyprosta-4,5,10,13-trans-tetraenoic acid,
8R-9α,15α-dihydroxy-20-bisnorprosta-4,5,10,13-trans-tetraenoic acid,
8R-9α,15α-dihydroxy-20-ethylprosta-4,5,10,13-trans-tetraenoic acid,
8R-9β,15α-dihydroxy-20-ethylprosta-4,5,10,13-trans-tetraenoic acid,
8R-9α,15α-dihydroxy-20-pentylprosta-4,5,10,13-trans-tetraenoic acid,
8R-4-methyl-9α,15α-dihydroxyprosta-4,5,10,13-trans-tetraenoic acid,
8R-6-methyl-9α,15α-dihydroxyprosta-4,5,10,13-trans-tetraenoic acid,
8R-4,6-dimethyl-9α,15α-dihydroxyprosta-4,5,10,13-trans-tetraenoic acid,
8R-4,6,15β-trimethyl-9α,15α-dihydroxyprosta-4,5,10,13-trans-tetraenoic acid,
8R-4-methyl-9β,15α-dihydroxyprosta-4,5,10,13-trans-tetraenoic acid,
8R-6-methyl-9β,15α-dihydroxyprosta-4,5,10,13-trans-tetraenoic acid,
8R-4,6-dimethyl-9β,15α-dihydroxyprosta-4,5,10,13-trans-tetraenoic acid,
8R-4,6,15β-trimethyl-9β,15α-dihydroxyprosta-4,5,10,13-trans-tetraenoic acid,
8R-6-methyl-9α,15α-dihydroxy-20-ethylprosta-4,5,10,13-trans-tetraenoic acid,
8R-6,20-dimethyl-9β,15α-dihydroxyprosta-4,5,10,13-trans-tetraenoic acid,
8R-15β-methyl-9α,15α-dihydroxyprosta-4,5,10,13-trans-tetraenoic acid,
8R-4-propyl-6,15β-dimethyl-9α,15α-dihydroxyprosta-4,5,10,13-trans-tetraenoic acid,
8R-15β-methyl-9β,15α-dihydroxy-20-ethylprosta-4,5,10,13-trans-tetraenoic acid,
15β-methyl-9α,15α-dihydroxyprosta-4,5,8(12),13-trans-tetraenoic acid,
4,6,15β-trimethyl-9α,15α-dihydroxyprosta-4,5,8(12),13-trans-tetraenoic acid,
4,6,15β-trimethyl-9β,15α-dihydroxyprosta-4,5,8(12),13-trans-tetraenoic acid,
15β-ethyl-9β,15α-dihydroxyprosta-4,5,8(12),13-trans-tetraenoic acid,
15β-propyl-9α,15α-dihydroxyprosta-4,5,8(12),13-trans-tetraenoic acid,
8R-9β-methyl-9α,15α-dihydroxyprosta-4,5,10,13-trans-tetraenoic acid,
8R-9β-methyl-9α,15α-dihydroxy-20-bisnorprosta-4,5,10,13-trans-tetraenoic acid,
8R-9β-methyl-9α,15α-dihydroxy-20-ethylprosta-4,5,10,13-trans-tetraenoic acid,
8R-9β-ethyl-9α,15α-dihydroxy-20-pentylprosta-4,5,10,13-trans-tetraenoic acid,
8R-4,9β-dimethyl-9α,15α-dihydroxyprosta-4,5,10,13-trans-tetraenoic acid,
8R-6,9,β-dimethyl-9α,15α-dihydroxyprosta-4,5,10,13-trans-tetraenoic acid,
8R-4,6,9β,15β-tetramethyl-9α,15α-dihydroxyprosta-4,5,10,13-trans-tetraenoic acid,
8R-4,6,9β-trimethyl-9α,15α-dihydroxyprosta-4,5,10,13-trans-tetraenoic acid,
8R-6,20-dimethyl-9β-propyl-9α,15α-dihydroxyprosta-4,5,10,13-trans-tetraenoic acid, and
8R-9β-ethyl-15β-methyl-9α,15α-dihydroxyprosta-4,5,10,13-trans-tetraenoic acid;
as well as the 9α-alkyl-9β-hydroxy and/or 15α-alkyl-15β-hydroxy isomers of the compounds having said substitution.

EXAMPLE 13

A. To a solution of 362 mg. of 9α,15α-dihydroxy-prosta-4,5,8(12),13-trans-tetraenoic acid methyl ester in 40 ml. of methanol is added a solution of 80 mg. of sodium hydroxide dissolved in 2 ml. of water, and the reaction mixture is stirred at room temperature for 2 hours. It is then poured into water and extracted twice with ethyl acetate to isolate the unsaponifiable products. The aqueous phase is cooled to 0°C, acidified with 10% hydrochloric acid and extracted three times with ethyl acetate. The combined extracts are washed with 50% saturated sodium chloride solution, dried over magnesium sulfate and evaporated to dryness under reduced pressure, thus obtaining 9α,15α-dihydroxyprosta-4,5,8(12),13-trans-tetraenoic acid (VI, R, R⁵ and R⁴' = H;

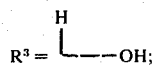

n = 4).

B. Twenty milligrams of 9α,15α-dihydroxyprosta-4,5,8(12),13-trans-tetraenoic acid methyl ester are dissolved in a mixture of 2 ml. of methanol, 2 ml. of water and 90 mg. of potassium carbonate. The reaction mixture is maintained at 40°C for 16 hours under nitrogen atmosphere, 10 ml. of water are then added, and the reaction mixture is then evaporated under reduced pressure to half volume. It is then acidified with 2N hydrochloric acid to pH 2 and extracted several times with ethyl acetate. The combined organic extracts are washed with water, dried over magnesium sulfate and evaporated to dryness under reduced pressure, thus obtaining 9α,15α-dihydroxyprosta-4,5,8(12),13-trans-tetraenoic acid, identical to the product obtained in part A.

In a similar manner, by following the methods described in parts A or B of this Example, from the corresponding esters of prosta-4,5,8(12),13-trans-tetraenoic acid derivatives prepared as described in Examples 8, 9 and 11, there are obtained the corresponding free acids, e.g.:

9β,15α-dihydroxyprosta-4,5,8(12),13-trans-tetraenoic acid,
4-methyl-9α,15α-dihydroxyprosta-4,5,8(12),13-trans-tetraenoic acid,
4-ethyl-9α,15α-dihydroxyprosta-4,5,8(12),13-trans-tetraenoic acid,
6-methyl-9α,15α-dihydroxyprosta-4,5,8(12),13-trans-tetraenoic acid,
4,6-dimethyl-9α,15α-dihydroxyprosta-4,5,8(12),13-trans-tetraenoic acid,
4,6,9β-trimethyl-9α,15α-dihydroxyprosta-4,5,8(12),13-trans-tetraenoic acid,
4-methyl-9β,15α-dihydroxyprosta-4,5,8(12),13-trans-tetraenoic acid,
6-methyl-9β,15α-dihydroxyprosta-4,5,8(12),13-trans-tetraenoic acid,
4,6-dimethyl-9β,15α-dihydroxyprosta-4,5,8(12),13-trans-tetraenoic acid,
9β,15α-dihydroxy-20-bisnorprosta-4,5,8(12),13-trans-tetraenoic acid,
9β,15α-dihydroxy-20-ethylprosta-4,5,8(12),13-trans-tetraenoic acid,
9β-methyl-9α,15α-dihydroxyprosta-4,5,8(12),13-trans-tetraenoic acid,
9β-propyl-9α,15α-dihydroxyprosta-4,5,8(12),13-trans-tetraenoic acid,
4,9β-diethyl-9α,15α-dihydroxyprosta-4,5,8(12),13-trans-tetraenoic acid,
9β-methyl-9α,15α-dihydroxy-20-ethylprosta-4,5,8(12),13-trans-tetraenoic acid,
4,9β-dimethyl-9α,15α-dihydroxy-20-ethylprosta-4,5,8(12),13-trans-tetraenoic acid, and
6,9β-dimethyl-9α,15α-dihydroxyprosta-4,5,8(12),13-trans-tetraenoic acid,
as well as the 9α-alkyl-9β-hydroxy isomers of the compounds having said substitution.

Alternatively, the hydrolysis of the alkyl ester group can be effected by the method described in Example 12.

EXAMPLE 14

By following the method of Example 2, 100 mg. of 9-keto-11α,15α-dihydroxyprosta-4,5,13-trans-trienoic acid are converted into 9-keto-15α-hydroxyprosta-4,5,10,13-trans-tetraenoic acid (II, R, R⁵ and R⁴' = H;

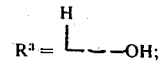

n = 4). Similarly, 4-methyl-9-keto-11α,15α-dihydroxyprosta-4,5,13-trans-trienoic acid,
6-methyl-9-keto-11α,15α-dihydroxyprosta-4,5,13-trans-trienoic acid,
4,6-dimethyl-9-keto-11α,15α-dihydroxyprosta-4,5,13-trans-trienoic acid,
9-keto-11α,15α-dihydroxy-20-ethylprosta-4,5,13-trans-trienoic acid,
4,20-dimethyl-9-keto-11α,15α-dihydroxyprosta-4,5,13-trans-trienoic acid and
9-keto-11α,15α-dihydroxy-20-norprosta-4,5,13-trans-trienoic acid,
are converted respectively into
4-methyl-9-keto-15α-hydroxyprosta-4,5,10,13-trans-tetraenoic acid,
6-methyl-9-keto-15α-hydroxyprosta-4,5,10,13-trans-tetraenoic acid,
4,6-dimethyl-9-keto-15α-hydroxyprosta-4,5,10,13-trans-tetraenoic acid,
9-keto-15α-hydroxy-20-ethylprosta-4,5,10,13-trans-tetraenoic acid,
4,20-dimethyl-9-keto-15α-hydroxyprosta-4,5,10,13-trans-tetraenoic acid and
9-keto-15α-hydroxy-20-norprosta-4,5,10,13-trans-tetraenoic acid.

EXAMPLE 15

By following the method of Example 3, 9-keto-11α,15α-dihydroxy-15β-methylprosta-4,5,13-trans-trienoic acid is converted into:
9-keto-15β-methyl-15α-hydroxyprosta-4,5,10,13-trans-tetraenoic acid (II, R, R⁵ and R⁴' = H;

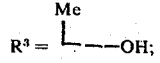

n = 4), obtaining a small quantity of 9-keto-15β-methyl-15α-hydroxyprosta-4,5,8(12),13-trans-tetraenoic acid as by-product.

Similarly,
4,15β-dimethyl-9-keto-11α,15α-dihydroxyprosta-4,5,13-trans-trienoic acid,
6,15β-dimethyl-9-keto-11α,15α-dihydroxyprosta-4,5,13-trans-trienoic acid,
4,6,15β-trimethyl-9-keto-11α,15α-dihydroxyprosta-4,5,13-trans-trienoic acid,
15β-methyl-9-keto-11α,15α-dihydroxy-20-ethylprosta-4,5,13-trans-trienoic acid,
4,15β-dimethyl-9-keto-11α,15α-dihydroxy-20-ethylprosta-4,5,13-trans-trienoic acid,
6,15β-dimethyl-9-keto-11α,15α-dihydroxy-20-ethylprosta-4,5,13-trans-trienoic acid, 6,15β-dimethyl-9-keto-11α,15α-dihydroxy-20-nor-prosta-4,5,13-trans-trienoic acid, 4-propyl-6,15β-dimethyl-9-keto-11α,15α-dihydroxyprosta-4,5,13-trans-trienoic acid, 15β-ethyl-9-keto-11α,15α-dihydroxyprosta-4,5,13-trans-trienoic acid and 15β-propyl-9-keto-11α,15α-dihydroxyprosta-4,5,13-trans-trienoic acid are converted respectively into:

4,15β-dimethyl-9-keto-15α-hydroxyprosta-4,5,10,13-trans-tetraenoic acid, 6,15β-dimethyl-9-keto-15α-hydroxyprosta-4,5,10,13-trans-tetraenoic acid, 4,6,15β-trimethyl-9-keto-15α-hydroxyprosta-4,5,10,13-trans-tetraenoic acid, 15β-methyl-9-keto-15α-hydroxy-20-ethylprosta-4,5,10,13-trans-tetraenoic acid, 4,15β-dimethyl-9-keto-15α-hydroxy-20-ethylprosta-4,5,10,13-trans-tetraenoic acid, 6,15β-dimethyl-9-keto-15α-hydroxy-20-ethylprosta-4,5,10,13-trans-tetraenoic acid, 6,15β-dimethyl-9-keto-15α-hydroxy-20-norprosta-4,5,10,13-trans-tetraenoic acid, 4-propyl-6,15β-dimethyl-9-keto-15α-hydroxyprosta-4,5,10,13-trans-tetraenoic acid, 15β-ethyl-9-keto-15α-hydroxyprosta-4,5,10,13-trans-tetraenoic acid, 15β-propyl-9-keto-15α-hydroxyprosta-4,5,10,13-trans-tetraenoic acid, obtaining in each case small amounts of the corresponding prosta-4,5,8(12),13-trans-tetraenoic acid compounds.

Likewise, the corresponding 15α-alkyl-15β-hydroxyprosta-4,5,13-trans-trienoic acids are converted into the respective 15α-alkyl-15β-hydroxyprosta-4,5,10,13-trans-tetraenoic acid derivatives as main products.

EXAMPLE 16

In accordance with the method of Example 7, 100 mg. of 9-keto-15α-hydroxyprosta-4,5,10,13-trans-tetraenoic acid are converted into its methyl ester, which upon reduction with sodium borohydride in methanol solution, in accordance with the method of Example 8, affords 9α,15α-dihydroxyprosta-4,5,10,13-trans-tetraenoic acid methyl ester and 9β,15α-dihydroxyprosta-4,5,10,13-trans-tetraenoic acid methyl ester (IV, R and $R^5$ = H;

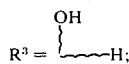

$R^{4'}$ = Me; $n$ = 4), separating the individual isomers by chromatography on silica gel.

Similarly, the remaining compounds obtained in Example 14 and the compounds obtained in Example 15 are converted into the corresponding esterified dihydroxylated derivatives, namely:

4-methyl-9α,15α-dihydroxyprosta-4,5,10,13-trans-tetraenoic acid methyl ester and 4-methyl-9β,15α-dihydroxyprosta-4,5,10,13-trans-tetraenoic acid methyl ester;

6-methyl-9α,15α-dihydroxyprosta-4,5,10,13-trans-tetraenoic acid methyl ester and 6-methyl-9β,15α-dihydroxyprosta-4,5,10,13-trans-tetraenoic acid methyl ester;

4,6-dimethyl-9α,15α-dihydroxyprosta-4,5,10,13-trans-tetraenoic acid methyl ester and 4,6-dimethyl-9β,15α-dihydroxyprosta-4,5,10,13-trans-tetraenoic acid methyl ester;

9α,15α-dihydroxy-20-ethylprosta-4,5,10,13-trans-tetraenoic acid methyl ester and 9β,15α-dihydroxy-20-ethylprosta-4,5,10,13-trans-tetraenoic acid methyl ester;

4,20-dimethyl-9α,15α-dihydroxyprosta-4,5,10,13-trans-tetraenoic acid methyl ester and 4,20-dimethyl-9β,15α-dihydroxyprosta-4,5,10,13-trans-tetraenoic acid methyl ester;

9α,15α-dihydroxy-20-norprosta-4,5,10,13-trans-tetraenoic acid methyl ester and 9β,15α-dihydroxy-20-norprosta-4,5,10,13-trans-tetraenoic acid methyl ester;

15β-methyl-9α,15α-dihydroxyprosta-4,5,10,13-trans-tetraenoic acid methyl ester and 15β-methyl-9β,15α-dihydroxyprosta-4,5,10,13-trans-tetraenoic acid methyl ester;

4,15β-dimethyl-9α,15α-dihydroxyprosta-4,5,10,13-trans-tetraenoic acid methyl ester and 4,15β-dimethyl-9β,15α-dihydroxyprosta-4,5,10,13-trans-tetraenoic acid methyl ester;

6,15β-dimethyl-9α,15α-dihydroxyprosta-4,5,10,13-trans-tetraenoic acid methyl ester and 6,15β-dimethyl-9β,15α-dihydroxyprosta-4,5,10,13-trans-tetraenoic acid methyl ester;

4,6,15β-trimethyl-9α,15α-dihydroxyprosta-4,5,10,13-trans-tetraenoic acid methyl ester and 4,6,15β-trimethyl-9β,15α-dihydroxyprosta-4,5,10,13-trans-tetraenoic acid methyl ester;

15β-methyl-9α,15α-dihydroxy-20-ethylprosta-4,5,10,13-trans-tetraenoic acid methyl ester and 15β-methyl-9β,15α-dihydroxy-20-ethylprosta-4,5,10,13-trans-tetraenoic acid methyl ester;

4,15β-dimethyl-9α,15α-dihydroxy-20-ethylprosta-4,5,10,13-trans-tetraenoic acid methyl ester and 4,15β-dimethyl-9β,15α-dihydroxy-20-ethylprosta-4,5,10,13-trans-tetraenoic acid methyl ester;

6,15β-dimethyl-9α,15α-dihydroxy-20-ethylprosta-4,5,10,13-trans-tetraenoic acid methyl ester and 6,15β-dimethyl-9β,15α-dihydroxy-20-ethylprosta-4,5,10,13-trans-tetraenoic acid methyl ester;

6,15β-dimethyl-9α,15α-dihydroxy-20-norprosta-4,5,10,13-trans-tetraenoic acid methyl ester and 6,15β-dimethyl-9β,15α-dihydroxy-20-norprosta-4,5,10,13-trans-tetraenoic acid methyl ester;

4-propyl-6,15β-dimethyl-9α,15α-dihydroxyprosta-4,5,10,13-trans-tetraenoic acid methyl ester and 4-propyl-6,15β-dimethyl-9β,15α-dihydroxyprosta-4,5,10,13-trans-tetraenoic acid methyl ester;

15β-ethyl-9α,15α-dihydroxyprosta-4,5,10,13-trans-tetraenoic acid methyl ester and 15β-ethyl-9β,15α-dihydroxyprosta-4,5,10,13-trans-tetraenoic acid methyl ester; and 15β-propyl-9α,15α-dihydroxyprosta-4,5,10,13-trans-tetraenoic acid methyl ester and 15β-propyl-9β,15α-dihydroxyprosta-4,5,10,13-trans-tetraenoic acid methyl ester, as well as the corresponding 15α-alkyl-15β-hydroxy isomers of the compounds having said substitution.

EXAMPLE 17

In accordance with the method of Example 9, 9-keto-15α-hydroxyprosta-4,5,10,13-trans-tetraenoic acid methyl ester is treated with 12 molar equivalents of methyl magnesium bromide, to yield 9β-methyl-9α,15α-dihydroxyprosta-4,5,10,13-trans-tetraenoic acid methyl ester and a small amount of 9α-methyl-9β,15α-dihydroxyprosta-4,5,10,13-trans-tetraenoic acid methyl ester (V, R and $R^5$ = H; $R^2$ and $R^{4'}$ = Me;

$$R^3 = \overset{H}{\underset{|}{L}} \text{---OH};$$

n = 4), which are separated by thin layer chromatography.

By the same method but using ethylmagnesium bromide and propylmagnesium bromide in place of methylmagnesium bromide there are respectively produced:

9β-ethyl-9α,15α-dihydroxyprosta-4,5,10,13-trans-tetraenoic acid methyl ester and 9β-propyl-9α,15α-dihydroxyprosta-4,5,10,13-trans-tetraenoic acid methyl ester, obtaining in each case small amounts of the corresponding 9α-ethyl(propyl)-9β-hydroxy isomers.

In a similar manner, starting from the corresponding 9keto-prostatetraenoic acid methyl ester compounds there are obtained:

4,9β-dimethyl-9α,15α-dihydroxyprosta-4,5,10,13-trans-tetraenoic acid methyl ester, 6,9β-dimethyl-9α,15α-dihydroxyprosta-4,5,10,13-trans-tetraenoic acid methyl ester, 4,6,9β-trimethyl-9α,15α-dihydroxyprosta-4,5,10,13-trans-tetraenoic acid methyl ester, 4,6,9β,15β-tetramethyl-9α,15α-dihydroxyprosta-4,5,10,13-trans-tetraenoic acid methyl ester, and 9β-methyl-9α,15α-dihydroxy-20-ethylprosta-4,5,10,13-trans-tetraenoic acid methyl ester, as main products, with small quantities of the corresponding 9α-methyl- 9β-hydroxy isomers.

EXAMPLE 18

A mixture of 90 mg. of 9α,15α-dihydroxyprosta-4,5,10,13-trans-tetraenoic acid methyl ester, 1.8 g. of dry, finely ground freshly extracted residue of the gorgonian *Plexaura homomalla* (Espero), [which results after extraction of the prostaglandin derivatives contained originally by this gorgonian, as described by A. Prince et al, in *Prostaglandins*, Vol 3, No. 4, p. 531 (1973)] and 10 ml. of a 0.1M sodium chloride and 0.05M calcium chloride solution in water is stirred at room temperature for 24 hours, maintaining the pH of the reaction mixture at 7.5–7.7 by addition of 0.1N sodium hydroxide solution. At the end of this time the reaction mixture is diluted with 15 ml. of acetone, adjusting the pH to 4, with dilute hydrochloric acid. Charcoal is added to decolorize the solution, and the insoluble material separated by filtration through Celite, diatomaceous earth, washing the solids with several portions of acetone. The combined filtrates are concentrated under reduced pressure to a small volume, and the product extracted from the aqueous residue with methylene chloride. The combined organic extracts are dried over magnesium sulfate and evaporated to dryness under reduced pressure. The oily residue is purified by t.l.c., thus obtaining the pure 9α,15α-dihydroxyprosta-4,5,10,13-trans-tetraenoic acid.

By following the above-described procedure or the procedure of Example 12, the remaining methyl ester compounds of Example 16 and those of Example 17 are converted into the corresponding free acids.

EXAMPLE 19

A mixture of 100 mg. of 8R-9α,15α-dihydroxyprosta-4,5,10,13-trans-tetraenoic acid, 0.4 ml. of pyridine and 0.8 ml. of acetic anhydride is kept at room temperature for 1 hour. The reaction mixture is then evaporated to dryness under reduced pressure and the residue is dissolved in ethyl acetate. Fifty milligrams of sodium bisulfate are added and the solution is filtered through Celite, diatomaceous earth. The filtrate is evaporated to dryness under reduced pressure to yield 8R-9α,15α-diacetoxyprosta-4,5,10,13-trans-tetraenoic acid.

By the same process but using propionic, caproic and cyclopentylpropionic anhydrides as esterifying agents there are produced the dipropionate, dicaproate and dicyclopentylpropionate of 8R-9α,15α-dihydroxyprosta-4,5,10,13-trans-tetraenoic acid.

In a similar manner 9α,15α-dihydroxyprosta-4,5,8(12),13-trans-tetraenoic acid, 8R-4-methyl-9α,15α-dihydroxyprosta-4,5,10,13-trans-tetraenoic acid methyl ester, 8R-6-methyl-9β,15α-dihydroxyprosta-4,5,10,13-trans-tetraenoic acid methyl ester, 8R-9-keto-15α-hydroxyprosta-4,5,10,13-trans-tetraenoic acid, 9-keto-15α-hydroxyprosta-4,5,8(12),13-trans-tetraenoic acid, 8R-4-methyl-9-keto-15α-hydroxyprosta-4,5,10,13-trans-tetraenoic acid, 4,6-dimethyl-9-keto-15α-hydroxyprosta-4,5,8(12),13-trans-tetraenoic acid, 8R-9-keto-15α-hydroxy-20-bisnorprosta-4,5,10,13-trans-tetraenoic acid.

9-keto-15α-hydroxy-20-ethylprosta-4,5,8(12),13-trans-tetraenoic acid,

9α,15α-dihydroxyprosta-4,5,10,13-trans-tetraenoic acid, 9-keto-15α-hydroxyprosta-4,5,10,13-trans-tetraenoic acid, 4-methyl-9α,15α-dihydroxyprosta-4,5,10,13-trans-tetraenoic acid and 4,6-dimethyl-9-keto-15α-hydroxyprosta-4,5,10,13-trans-tetraenoic acid, are converted into the corresponding 9,15-diacyloxy or 15-monoacyloxy derivatives.

EXAMPLE 20

To a solution of 200 mg. of 8R-9-keto-15α-hydroxyprosta-4,5,10,13-trans-tetraenoic acid methyl ester in 5 ml. of methylene chloride are added 5 mg. of p-toluenesulfonic acid and 0.25 ml. of freshly distilled dihydropyran. The reaction mixture is stirred for 15 minutes at room temperature, a few drops of pyridine are added and diluted with ether. The ethereal solution is washed with 25 ml. of 50% aqueous sodium chloride solution and then with saturated sodium chloride solution. The organic phase is separated, dried over magnesium sulfate and evaporated to dryness under reduced pressure, at approximately 0°C. The oily residue is purified by thin-layer chromatography using chloroform-methanol (9:1) as eluant, to produce the pure 8R-9-keto-15α-tetrahydropyranyloxyprosta-4,5,10,13-trans-tetraenoic acid methyl ester.

In a similar manner but using dihydrofuran or 4-methoxy-5,6-dihydro-2H-pyran in place of dihydropyran, there are obtained 8R-9-keto-15α-tetrahydrofuranyloxyprosta-4,5,10,13-trans-tetraenoic acid methyl ester and 8R-9-keto-15α-(4-methoxytetrahydropyranyloxy)-prosta-4,5,10,13-trans-tetraenoic acid methyl ester.

Likewise, 9-keto-15α-hydroxyprosta-4,5,8(12),13-trans-tetraenoic acid, 4-methyl-9-keto-15α-hydroxyprosta-4,5,8(12),13-trans-tetraenoic acid,

43

8R-6-methyl-9-keto-15α-hydroxyprosta-4,5,10,13-trans-tetraenoic acid,
4,6-dimethyl-9-keto-15α-hydroxyprosta-4,5,8(12),13-trans-tetraenoic acid,
8R-9-keto-15α-hydroxy-20-ethylprosta-4,5,10,13-trans-tetraenoic acid,
9-keto-15α-hydroxyprosta-4,5,10,13-trans-tetraenoic acid and
4,6-dimethyl-9-keto-15α-hydroxyprosta-4,5,10,13-trans-tetraenoic acid are converted into the corresponding 15α-tetrahydropyranyloxy, 15α-tetrahydrofuranyloxy and 15α(4-methoxy)-tetrahydropyranyloxy derivative.

By the same method but using twice the amount of the etherifying agents,
8R-9β,15α-dihydroxyprosta-4,5,10,13-trans-tetraenoic acid methyl ester,
8R-4,6-dimethyl-8α,15α-dihydroxyprosta-4,5,10,13-trans-tetraenoic acid methyl ester and
9α,15α-dihydroxyprosta-4,5,8(12),13-trans-tetraenoic acid are converted into the corresponding 9,15-bistetrahydropyranyloxy, 9,15-bistetrahydrofuranyloxy and 9,15-bis(4-methoxy)-tetrahydropyranyloxy derivatives.

EXAMPLE 21

To a solution of 100 mg. of 9α,15α-dihydroxyprosta-4,5,8(12),13-trans-tetraenoic acid in 10 ml. of methanol is added 3.4 ml. of a 0.1N solution of sodium hydroxide, and the mixture is stirred at room temperature for 30 minutes. It is then evaporated to dryness under reduced pressure, to give the sodium salt of 9α,15α-dihydroxyprosta-4,5,8(12),13-trans-tetraenoic acid.

By employing 1.1 molar equivalents of potassium hydroxide (in the form of a 0.1N solution) in place of sodium hydroxide in the above procedure, the potassium salt of 9α,15α-dihydroxyprosta-4,5,8(12),13-trans-tetraenoic acid is obtained.

Similarly, the sodium and potassium salts of the other free prostaglandin derivatives obtained in Examples 1, 2, 3, 4, 5, 6, 12, 13, 14, 15 and 18 can be produced.

EXAMPLE 22

To a solution of 100 mg. of 8R-9α,15α-dihydroxyprosta-4,5,10,13-trans-tetraenoic acid in 10 ml. of methanol is added a mixture of 3 ml. of concentrated ammonium hydroxide solution and 5 ml. of methanol. The resulting mixture is stirred for two hours at room temperatures and then evaporated to dryness, to yield the ammonium salt of 8α-9α,15α-dihydroxyprosta-4,5,10,13-trans-tetraenoic acid.

By employing the theoretical amounts of dimethylamine, diethylamine, dipropylamine or tris(hydroxyethyl)amine in place of ammonium hydroxide, the corresponding salts of 8R-9α,15α-dihydroxyprosta-4,5,10,13-trans-tetraenoic acid are obtained.

In a similar manner, the ammonia, dimethylamine, diethylamine, dipropylamine and tris(hydroxyethyl)amine salts of other free prostaglandin derivatives of the previous Examples are obtained.

We claim:

1. A racemic compound selected from the group of those represented by the following formula:

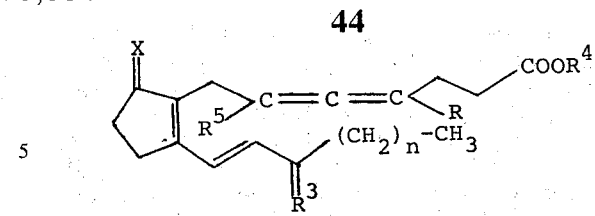

wherein X is a keto group;
each of R and $R^5$ is hydrogen, methyl, ethyl or propyl;
$R^3$ is the grouping

in which $R^1$ is hydrogen, tetrahydrofuran-2-yloxy, tetrahydropyran-2-yloxy, 4-methoxytetrahydropyran-4-yloxy, a hydrocarbon carboxylic acyloxy group containing from 1 to 12 carbon atoms or a substituted hydrocarbon carboxylic acyloxy group having from 1 to 12 carbon atoms wherein the substituent is selected from the group consisting of hydroxy, alkoxy containing up to twelve carbon atoms, nitro, amino and halogen, or the grouping

in which $R^6$ is methyl, ethyl or propyl;
$R^4$ is hydrogen, a lower alkyl group of 1 to 3 carbon atoms or the pharmaceutically acceptable, non-toxic salts of compounds in which
$R^4$ is hydrogen;
$n$ is an integer of from 2 to 9;
and the wavy lines } indicate the α or β configuration or mixtures thereof;
provided that when $R^6$ is α the hydroxyl group, attached to the same carbon atom as $R^6$, is β; and when $R^6$ is β the hydroxyl group, attached to the same carbon atom as $R^6$, is α.

2. A compound according to claim 1 wherein $R^4$ is hydrogen.
3. A compound according to claim 1 wherein R, $R^4$ and $R^5$ are hydrogen.
4. A compound according to claim 1 wherein R and $R^4$ are hydrogen and $R^5$ is methyl, ethyl or propyl.
5. A compound according to claim 1 wherein $R^4$ and $R^5$ are hydrogen and R is methyl, ethyl or propyl.
6. A compound according to claim 1 wherein $R^3$ is α-hydroxy-β-hydrogen and $R^4$ is hydrogen.
7. A compound according to claim 1 wherein $R^3$ is the grouping

and $R^4$ is hydrogen.
8. A compound according to claim 1 wherein $n$ is 4.
9. A compound according to claim 1 wherein $n$ is 6.
10. A compound according to claim 1 wherein R, $R^4$ and $R^5$ are hydrogen, $R^3$ is α-hydroxy-β-hydrogen and $n$ is 4, 9-keto-15α-hydroxyprosta-4,5,8(12),13-trans-tetraenoic acid and the non-toxic, pharmaceutically acceptable salts thereof.

11. A compound according to claim 1 wherein R and $R^5$ are hydrogen, $R^3$ is α-hydroxy-β-hydrogen, $R^4$ is methyl and $n$ is 4, 9-keto-15α-hydroxyprosta-4,5,8(12),13-trans-tetraenoic acid methyl ester.

12. A compound according to claim 1 wherein R is methyl, $R^4$ and $R^5$ are hydrogen, $R^3$ is α-hydroxy-β-hydrogen and $n$ is 4, 4-methyl-9-keto-15α-hydroxyprosta-4,5,8(12),13-trans-tetraenoic acid and the non-toxic, pharmaceutically salts thereof.

13. A compound according to claim 1 wherein R and $R^4$ are hydrogen, $R^3$ is α-hydroxy-β-hydrogen, $R^5$ is methyl and $n$ is 4, 6-methyl-9-keto-15α-hydroxyprosta-4,5,8(12),13-trans-tetraenoic acid and the non-toxic pharmaceutically acceptable salts thereof.

14. A compound according to claim 1 wherein R and $R^5$ are methyl, $R^3$ is α-hydroxy-β-hydrogen, $R^4$ is hydrogen and $n$ is 4, 4,6-dimethyl-9-keto-15α-hydroxyprosta-4,5,8(12),13-trans-tetraenoic acid and the non-toxic, pharmaceutically acceptable salts thereof.

15. A compound according to claim 1 wherein R, $R^4$ and $R^5$ are hydrogen, $R^3$ is the grouping

and $n$ is 4, 9-keto-15}-methyl-15}-hydroxyprosta-4,5,8(12),13-trans-tetraenoic acid and the non-toxic, pharmaceutically acceptable salts thereof.

16. A compound according to claim 1 wherein R is methyl, $R^4$ and $R^5$ are hydrogen, $R^3$ is the grouping

and $n$ is 4, 4,15}-dimethyl-9-keto-15}-hydroxyprosta-4,5,8(12),13-trans-tetraenoic acid and the non-toxic, pharmaceutically acceptable salts thereof.

17. A compound according to claim 1 wherein R and $R^1$ are hydrogen, $R^3$ is the grouping

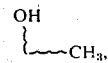

$R^5$ is methyl and $n$ is 4, 6,15}-dimethyl-9-keto-15}-hydroxyprosta-4,5,8(12),13-trans-tetraenoic acid and the non-toxic, pharmaceutically acceptable salts thereof.

18. A compound according to claim 1 wherein R and $R^5$ are methyl, $R^3$ is the grouping

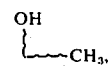

$R^4$ is hydrogen and $n$ is 4, 4,6,15}-trimethyl-9-keto-15}-hydroxyprosta-4,5,8(12),13-trans-tetraenoic acid and the non-toxic, pharmaceutically acceptable salts thereof.

19. A compound according to claim 1 wherein R, $R^4$ and $R^5$ are hydrogen, $R^3$ is α-hydroxy-β-hydrogen and $n$ is 6, 9-keto-15α-hydroxy-20-ethylprosta-4,5,8(12),13-trans-tetraenoic acid and the non-toxic, pharmaceutically acceptable salts thereof.

* * * * *